(12) United States Patent
Haynie

(10) Patent No.: US 7,550,557 B2
(45) Date of Patent: Jun. 23, 2009

(54) MULTILAYER FILMS, COATINGS, AND MICROCAPSULES COMPRISING POLYPEPTIDES

(75) Inventor: Donald T. Haynie, New Haven, CT (US)

(73) Assignee: Louisiana Tech University Foundation, Inc., Ruston, LA (US)

(*) Notice: Subject to any disclaimer, the term of this patent is extended or adjusted under 35 U.S.C. 154(b) by 429 days.

(21) Appl. No.: 11/586,329

(22) Filed: Oct. 25, 2006

(65) Prior Publication Data

US 2007/0077275 A1    Apr. 5, 2007

Related U.S. Application Data

(63) Continuation-in-part of application No. 10/652,364, filed on Aug. 29, 2003, now Pat. No. 7,348,399.

(60) Provisional application No. 60/729,828, filed on Oct. 25, 2005.

(51) Int. Cl.
C07K 17/00 (2006.01)
C07K 2/00 (2006.01)

(52) U.S. Cl. .................................................. 530/300

(58) Field of Classification Search .................. None
See application file for complete search history.

(56) References Cited

U.S. PATENT DOCUMENTS

| | | | |
|---|---|---|---|
| 5,138,026 A | 8/1992 | Miyasaka et al. | |
| 5,162,486 A | 11/1992 | Follmann et al. | |
| 5,686,113 A | 11/1997 | Speaker et al. | |
| 5,705,222 A | 1/1998 | Somasundaran et al. | |
| 5,747,334 A | 5/1998 | Kay et al. | |
| 6,020,175 A | 2/2000 | Onda et al. | |
| 6,022,500 A | 2/2000 | John et al. | |
| 6,107,084 A | 8/2000 | Onda et al. | |
| 6,268,222 B1 | 7/2001 | Chandler et al. | |
| 6,309,701 B1 | 10/2001 | Barbera-Guillem | |
| 6,316,084 B1 | 11/2001 | Claus et al. | |
| 6,437,095 B1 | 8/2002 | Lilie et al. | |
| 6,447,887 B1 | 9/2002 | Claus et al. | |
| 6,479,146 B1 | 11/2002 | Caruso et al. | |
| 6,485,703 B1 | 11/2002 | Cote et al. | |
| 6,699,501 B1 | 3/2004 | Neu et al. | |
| 6,743,321 B2 | 6/2004 | Guralski et al. | |
| 6,743,521 B2 | 6/2004 | Hubbell et al. | |
| 6,833,192 B1 | 12/2004 | Caruso et al. | |
| 6,989,267 B2 | 1/2006 | Kim et al. | |
| 7,045,146 B2 | 5/2006 | Caruso et al. | |
| 7,056,554 B2 | 6/2006 | Voigt et al. | |
| 7,101,575 B2 | 9/2006 | Donath et al. | |
| 2002/0037383 A1 | 3/2002 | Spillman, Jr. et al. | |
| 2003/0124368 A1 | 7/2003 | Lynn et al. | |
| 2003/0211129 A1 | 11/2003 | Spillman, Jr. et al. | |
| 2004/0013721 A1 | 1/2004 | Antipov et al. | |
| 2004/0013738 A1 | 1/2004 | Voigt et al. | |
| 2005/0037050 A1 | 2/2005 | Weber | |
| 2005/0058603 A1 | 3/2005 | Gao et al. | |
| 2005/0069950 A1 | 3/2005 | Haynie | |
| 2005/0129727 A1 | 6/2005 | Weber et al. | |
| 2005/0180945 A1 | 8/2005 | Chaikof et al. | |

FOREIGN PATENT DOCUMENTS

| | | |
|---|---|---|
| EP | 0 667 148 | 8/1985 |
| EP | 0 415 273 | 8/1990 |
| EP | 0 433 428 | 8/1991 |
| EP | 0 472 990 | 8/1991 |
| EP | 1 116 516 A1 | 7/2001 |
| EP | 0 823 331 | 11/2001 |
| GB | 2 135 954 | 9/1984 |
| WO | WO 99/47252 | 9/1999 |
| WO | WO 99/47253 | 9/1999 |
| WO | WO 00/03797 | 1/2000 |
| WO | WO 00/77281 A1 | 12/2000 |
| WO | WO 02/09864 | 2/2002 |
| WO | WO 02/09865 | 2/2002 |
| WO | WO 02/017888 A2 | 7/2002 |

OTHER PUBLICATIONS

Chluba et al. "Peptide Hormone Covalently Bound to Polyelectrolytes and Embedded into Multilayer Architectures Conserving Full Biological Activity," Biomacromolecules, 2001, 2, 800-5.*
Pishko et al. "Mass Transfer in Amperometric Biosensors Based on Nanocomposite Thin Films of Redox Polymers and Oxidoreductases," Sensors, 2002, 79-90.*
Lactate oxidase [gi:849022], http://www.ncbi.nlm.nih.gov/entrez/viewer.fcgi?db=protein&id=849022, printed Feb. 5, 2009.*
Glucose oxidase [gi:110294440], http://www.ncbi.nlm.nih.gov/entrez/viewer.fcgi?db=protein&id=110294440, printed Feb. 5, 2009.*
Pyruvate oxidase [gi:1009025], http://www.ncbi.nlm.nih.gov/entrez/viewer.fcgi?db=protein&id=1009025.*
Picart et al; "Primary Cell Adhesion on RGD-Functionalized and Covalently Crosslinked Thin Polyelectrolyte Multilayer Films"; Advanced Functional Materials; 15; pp. 83-94; (2005).
Tilman M. Hackeng et al; "Protein Synthesis by Native Chemical Ligation: Expanded Scope by Using Straightforward Methodology"; Proc. Natl. Acad. Sci.; USA; 96; pp. 10068-10073; (1999).

(Continued)

*Primary Examiner*—Cecilia Tsang
*Assistant Examiner*—Christina Marchetti Bradley
(74) *Attorney, Agent, or Firm*—Cantor Colburn LLP

(57) ABSTRACT

Disclosed herein are multilayer films comprising two or more layers of polyelectrolytes, wherein adjacent layers comprise oppositely charged polyelectrolytes. A first layer polypeptide comprising one or more first amino acid sequence motifs, wherein the one or more first amino acid sequence motifs has a length of 5 to 15 amino acids residues, and wherein the balance of charge in the first amino acid sequence motif at pH 7 is greater than or equal to approximately one-half of the length of the first amino acid sequence motif, wherein the first layer polypeptide is not a homopolymer. Further, a second layer comprises second layer polyelectrolyte comprising a nonprotein polyelectrolyte having a charge opposite that of the first layer polypeptide.

13 Claims, 13 Drawing Sheets

OTHER PUBLICATIONS

Michael S. Wong et al; "Assembly of Nanoparticles into Hollow Spheres Using Block Copolypeptides", Nano Letters; 2; pp. 583-587; (2002).

Glinel et al.; "Polyelectrolyte Multilayers Based on Amphiphilic Polysaccharides: Application for Entrapment and Release of Hydrophobic Molecules"; Abstracts of Papers, American Chemical Society; 230; p. 28; (2005).

Haynie, et al.; "Protein-Inspired Multilayer Nanofilms: Science, Technology and Medicine"; Nanomedicine: Nanotechnology, Biology, and Medicine; 2; pp. 150-157; (2006).

Li, et al; "Multilayer Biomimetics: Reversible Covalent Stabilization of a Nanostructured Biofilm"; Biomacromolecules; 5; pp. 1667-1670; (2004).

Zheng, et al; "Design of Peptides for Thin Films, Coatings and Microcapsules for Applications in Biotechnology"; Journal of Biomaterials Science Polymer Edition; 16; pp. 285-299; (2005).

International Search Report and Written Opinion; International Application No. PCT/US2006/041713; International Filing Date Oct. 25, 2006; Applicant's File Reference ATE-0002P2-PCT; Date of Mailing Apr. 23, 2008, 16 pages.

Chou Fasman Parameters, http://prowl.rockefeller.edu/aainfo/chou.htm; Jun. 29, 2008; 2 pages.

Pathak et al; "Structure of the B-Subunit of Translation Initiation Factor elF-2"; Cell; 54; pp. 633-639; CAS 1989: 167098; one page.

Konecki et al.; "The Primary Structure of Human Chromiogranin A and Pancreastatin"; J. Biol. Chem.; 262; pp. 17026-17030; (1987).

Arora, et al.; "Design of Artificial Transcriptional Activators with Rigid Poly-L-Proline Linkers"; J. Am. Chem. Soc.; 124; pp. 13067-13071; (2002).

Boulmedais, et al.; "Secondary Structure of Polypeptide Multilayer Films: An Example of Locally Ordered Polyelectrolyte Multilayers"; Langmuir; 18; pp. 4523-4525; (2002).

Cheng, et al.; "Ultrathin Polypeptide Multilayer Films for the Fabrication of Model Liquid/LiquidElectrochemical Interfaces"; J. Phys. Chem. B; 103; pp. 8726-8731; (1999).

Cooper, et al.; "Thermodynamic Consequences of the Removal of a Disulphide Bridge from Hen Lysozyme"; J. Mol. Bio. 225; pp. 939-943; (1991) Abstract Only.

Fermi, et al.; "The Crystal Structure of Human Deoxyhaemoglobin at 1.74 Å Resolution"; J. Mol. Biol.; 175; pp. 159-174; (1984).

Greaser; "Identification of New Repeating Motifs in Titin"; Proteins: Structure, Function, and Genetics; 43; pp. 145-149; (2001).

Hong, et al.; "The Effect of Charge Increase on the Specificity and Activity of a Short Antimicrobial Peptide"; Peptides; 22; pp. 1669-1674; (2001).

Hugli; "Human Anaphylatoxin (C3a) From the Third Component of Complement"; J. Biol. Chem.; 250; pp. 8293-8301; (1975).

Jöns, et al.; "Identification of the Binding Interface Involved in Linkage of Cytoskeletal Protein 4.1 to the Erythrocyte Anion Exchanger"; The EMBO Journal; 11; pp. 2863-2867; (1992).

Nagi; et al.; "An Inverse Correlation Between Loop Length and Stability in a Four-Helix-Bundle Protein"; Folding & Design; 2; pp. 67-75; (1997).

Ohkawa, et al.; "Biodegradation of Ornithine-Containing Polylysine Hydrogels"; Biomaterials; 19; pp. 1855-1860; (1998).

Oppenheim; et al.; "Histatins, A Novel Family of Histidine-Rich Proteins in Human Parotid Secretion"; J. Biol. Chem.; 263; pp. 7472-7477; (1988).

Qiu, et al.; "Studies on the Drug Release Properties of Polysaccharide Multilayers Encapsulated Ibuprofen Microparticles"; Langmuir; 17; pp. 5375-5380; (2001).

Rado, et al.; "Isolation of Lactoferrin cDNA From a Human Myeloid Library and Expression of mRNA During Normal and Leukemic Myelopoiesis"; Blood; 70; pp. 989-993; (1987).

Sauerbrey; The Use of Quartz Oscillators for Weighing Thin Layers and for Microweighting; Z. Physik; 155; pp. 206-222; (1959); Abstract only; 1 page.

Schierholz; et al.; "Implant infections: A Haven for Opportunistic Bacteria"; Journal of Hospital Infection; 49; pp. 87-93; (2001).

Sugimoto, et al.; "The Amino Acid Sequence of a Glutamic Acid-Rich Protein from Bovine Retina as Deduced from the cDNA Sequence"; Proc. Natl. Acad. Sci. USA; 88; pp. 3116-3119; (1991).

Verrecchio; et al.; "Design of Peptides with High Affinities for Heparin and Endothelial Cell Proteoglycans"; J. Biol. Chem.; 275; pp. 7701-7707; (2000).

Wadhwa; et al.; "Peptide-Mediated Gene Delivery: Influence of Peptide Structure on Gene Expression"; Bioconjugate Chem.; 8; pp. 81-88; (1997).

McKenzie et al., "A Potent New Class of Reductively Activated Peptide Gene Delivery Agents"; J. Biol. Chem.; 275; pp. 9970-9977; (2000).

Al, et al.; "Biomedical Applications of Electrostatic Layer-by-Layer Nano-Assembly of Polymers, Enzymes, and Nanoparticles"; Cell Biochemistry and Biophysics; 39; pp. 23-43, 2003.

Bachas, et al.; "Oriented Assembly of Proteins on Surfaces"; Proceedings of the First Joint Conference Serving Humanity, Advancing Technology; Oct. 10-16; Atlanta, GA; p. 739; 1999.

Chaudhuri, "Thiol/Disulphide Exchange Reaction: A Key Regulatory Process in Biological Systems"; Current Science; 68; pp. 692-698; 1995.

Huang, et al.; "Coating of Uniform Inorganic Particles with Polymers"; Journal of Colloid and Interface Science; 170; pp. 275-283; 1995.

Kawasaki, et al.; "Separation of Peptides on the Basis of the Difference in Positive Charge: Simultaneous Isolation of C-Terminal and Blocked N-Terminal Peptides From Tryptic Digests"; J. Biochem.; 102; pp. 393-400; 1987.

Liu, et al.; "Efficient Oligomerization of Negatively-Charged Beta-Amino Acids at -20 ° C."; J. Am. Chem. Soc.; 119; pp. 4791-4792; 1997.

Lvov, et al.; "Protein Architecture: Assembly of Ordered Films by Means of Alternated Adsorption of Oppositely Charged Macromolecules"; Membr. Cell Biol.; 11; pp. 277-303; 1997.

Puntervoll, et al.; "ELM Server: A New Resource for Investigating Short Functional Sites in Modular Eukaryotic Proteins"; Nucleic Acids Research; 31; pp. 3625-3630; 2003.

Simoncsits, et al.; "Covalent Joining of the Subunits of a Homodimeric Type II Restriction Endonuclease: Single-Chain Pvull Endonuclease"; J. Mol. Biol.; 309; pp. 89-97; 2001.

International Search Report; International Application No. PCT/US04/39209; International Filing Date Nov. 22, 2004; Applicant's File Reference 16675/98625; Date of Mailing Jul. 10, 2006.

Caruso, et al.; "Protein Multilayer Formation on Colloids Through a Stepwise Self-Assembly Technique"; J. Am. Chem. Soc.; 121; pp. 6039-6046; 1999.

Pastoriza-Santos, et al. "Core-Shell Colloids and Hollow Polyelectrolyte Capsules Based on Diazoresins." Adv. Funct. Matt. 2001, 11 (2), 122-128.

Gross & Farmer "Reduction-oxidation potential of blood as a function of partial pressure of oxygen." Nautre, 213 (77), 717-718, 1966.

G. Sukhurukov, et al. "Controlled Precipitation of Dyes into Hollow Polyelectrolyte Capsules Based on Colloids and Biocolloids" Adv. Mat., vol. 12 pp. 112-115 (2000).

Heather A. Clark, et al. "Optical Nanosensors for Chemical Analysis Inside Single Living Cells. 2. Sensors for pH and Calcium and the Intracellular Application of PEBBLE Sensors" Anal. Chem., vol. 71, pp. 4837-4843 (1999).

Concetta Tedeschi, et al. "Adsorption and Desorption Behavior of an Anionic Pyrene Chromophore in Sequentially Deposited Polyelectrolyte-Dye Thin Films" J. Am. Chem. Soc. 2000, 122.

A. J. Chung et al. "Methods of Loading and Releasing Low Molecular Weight Cationic Molecules in Weak Polyelectrolyte Multilayer Films" Langmuir 2002, 18.

Ajay J. Khopade, et al. "Electrostatically Assembled Polyelectrolyte/Dendrimer Multilayer Films as Ultrathin Nanoreservoirs" Nano Letters, 2002, vol. 2, No. 4.

Frank Caruso, et al. "Investigation of Electrostatic Interactions In Polyelectrolyte Multilayer Fims: Binding of Anionic Fluorescent Probes to Layers Assembled onto Colloids" Macromolecules 1999, 32.

Phillips, et al. "Polyethylene Glycol-Modified Liposome-Encapsulated Hemoglobin: A Long Circulating Red Cell Substitute" 1999, 288, pp. 665-670.

Zhang "Fabrication of novel biomaterials through molecular self-assembly" Nature Biotechnology, 2003, 21, pp. 1171-1178.

Kawahashi, et al. "Preparation and properties of uniform coated colloidal particles" Journal of Colloid and Interface Science, 1990, 138, pp. 534-542.

Philipse, et al. "Magnetic Silica Dispersions: Preparation and Stability of Surface-Modified Silica Particles with a Magnetic Core" Langmuir, 1994, 10, pp. 92-99.

Oyama, et al. "Coating of Uniform Inorganic Particles with Polymers, I" Journal of Colloid and Interface Science, 1993, 160, pp. 298-303 (abstract only).

Iller "Multilayers of Collodial Particles" Journal of Colloid and Interface Science, 1966, 21, pp. 569-594.

Kleinfeld, et al. "Stepwise Formation of Multilayered Nanostructural Films from Macromolecular Precursors" Science, 1994, 265, pp. 370-373.

Marzan, et al. "Synthesis of Nanosized Gold-Silica Core-Shell Particles" Langmuir, 1996, 12, pp. 4329-4335.

Giersig, et al. "Direct Observation of Chemical Reactions in Silica-Coated Gold and Silver Nanoparticles" Advanced Materials, 1997, 9, pp. 570-575.

Schmitt, et al. "Metal Nanoparticle/Polymer Superlattice Films: Fabrication and Control of Layer Structure" Advanced Materials, 1997, 9, pp. 61-65.

Lvov, et al. "Assembly of Multicomponent Protein Films by Means of Electrostatic Layer-by-Layer Adsorption" J. Am. Chem. Soc. 1995, 117, pp. 6117-6123.

Feldheim, et al. "Electron Transfer in Self-Assembled Inorganic Polyelectrolyte/Metal Nanoparticle Heterostructures" J. Amer. Chem. Soc., 1996, 118, pp. 7640-7641.

Sukhorukov, et al. "Assembly of polyelectrolyte multiplayer films by consecutively alternating adsorption of polynucleotides and polycations" Thin Solid Films, 1996, pp. 284-285, pp. 220-223.

Sukhorukov, et al. "Layer-by-layer self assembly of polyelectrolytes on colloidal particles" Colloids and Surfaces A, 1998, pp. 253-266.

Letter to the editor, "Preparation and Properties of Uniform Coated Colloidal Particles. VII. Silica on Hermatite" Journal of Colloid and Interface Science, 1992, 150, pp. 594-598.

Margel, et al. "Acrolein Polymerization: Monodisperse, Homo, and Hybrido Microspheres, Synthesis, Mechanism, and Reactions" Journal of Polymer Science: Polymer Chemistry Edition, 1984, 22, pp. 145-158.

Decher, et al. "New nanocomposite films for biosensors: layer-by-layer adsorbed films of polyelectrolytes, proteins or DNA" Biosensors & Bioelectronics, 1994, 9, pp. 677-684.

Furusawa, et al. "A method for preparing surfactant-free polystyrene lattices of high surface charge" Kolloid-Z. u.Z. Polymere, 1972, 250, pp. 908-909.

Tsukruk, et al. "Self-Assembled Multilayer Films from Dendrimers" Langmuir, 1997, 13, pp. 2171-2176.

Ariga, et al. "Assembling Alternate Dye-Polyion Molecular Films by Electrostatic Layer-by-Layer Adsorption" J. Amer. Chem. Soc., 1997, 119, pp. 2224-2231.

Keller, et al. "A New Series of Magnetic Rare Earth Cuprates: $RCu_2O_4$ (R=La, Nd, Sm, and Eu)" J. Amer. Chem. Soc., 1994, 116, pp. 8070-8076.

Keller, et al. "Layer-by-Layer Assembly of Intercalation Compounds and Heterostructures on Surfaces: Toward Molecular "Beaker" Epitaxy" J. Amer. Chem. Soc., 1994, 116, pp. 8817-8818.

Kotov, et al. "Mechanism of and Defect Formation in the Self-Assembly of Polymeric Polycation-Montmorillonite Ultrathin Films" J. Amer. Chem. Soc., 1997, 119, pp. 6821-6832.

Onda, et al. "Sequential Actions of Glucose Oxidase and Peroxidase in Molecular Films Assembled by Layer-by-Layer Alternate Adsorption" Biotechnology and Bioengineering, 1996, 51, pp. 163-167.

Araki, et al. "Layer-by-Layer Growth of Electrostatically Assembled Multilayer Porphyrin Films" Langmuir, 1996, 12, pp. 5393-5398.

Yoo, et al. "New Electro-Active Self-Assembled Multilayer Thin Films Based on Alternately Adsorbed Layers of Polyelectrolytes and Functional Dye Molecules" Synthetic Metals, 1997, 85, pp. 1425-1426.

Caruso, et al. "Nanoengineering of Inorganic and Hybrid Hollow Spheres by Colloidal Templating" www.sciencemag.org; Science. 1998, 282, pp. 1111-1114.

Keller, et al. "Photoinduced Charge Separation in Multilayer Thin Films Grown by Sequential Adsorption of Polyelectrolytes". J. Am. Chem. Soc. 1995, 117, pp. 12879-12880.

Chang. "Present Status of modified hemoglobin as blood substitutes and oral therapy for end stage renal failure using artificial cells containing genetically engineered cells". Ann N Y Acad Sci. 2001; 944, pp. 362-372. (Abstract Only).

Gero Decher. "Fuzzy Nanoassemblies: Toward Layered Polymeric Multicomposites" Science. 1997, 277, pp. 1232-1237.

Caruso, et al. "Assembly of Alternating Polyelectrolyte and Protein Multilayer Films for Immunosensing". Langmuir 1997, 13, pp. 3427-3433.

Lvov, Y. & Möhwald, H., "Electrostatic Layer-by-Layer Assembly of Proteins and Polyions" in *Protein Architecture: Interfacial Molecular Assembly and Immobilization Biotechnology*, eds. (New York: Marcel Dekker, 1999), pp. 125-167.

Angeletti, R.H. (1999) "Design of Useful Peptide Antigens," *J. Biomol. Tech.* 10:2-10.

Chou, P. and Fasman, G., "Conformational Parameters for Amino Acids in Helical, Beta-Sheet, and Random Coil Regions Calculated from Proteins," *Biochemistry* 13:211 (1974).

Caruso, F., Niikura, K., Furlong, N. and Okahata, "Assembly of Alternating Polyelectrolyte and Protein Multilayer Films for Immunosensing," (1997) *Langmuir* 13:3427.

Caruso, F., Furlong, N., Ariga, K., Ichinose, I., and Kunitake, T., "Characterization of Polyelectrolyte-Protein Multilayer Films by Atomic Force Microscopy, Scanning Electron Microscopy, and Fourier Transform Infrared Reflection-Adsorption Spectroscopy," (1998) *Langmuir* 14:4559.

Lvov, Y., Atnipov, A., Mamedoc, A., Mohwald, H., Sukhorukov, G., "Urease Encapsulation in Nanoorganized Microshells," (2001) *Nano Letters* vol. 1, No. 3, pp. 125-128.

Pargaonkar, N.A., G. Sharma, and K.K. Vistakula. (2001) "Artificial Blood: Current Research Report".

Scott, Mark D., Murad, K., Koumpouras, F., Talbot, M., Eaton, J., "Chemical camouflage of antigenic determinants: Stealth erythrocytes," (1997) *Proc. Natl. Acad. Sci. USA*. 94 (14): 7566-7571.

Nester, T. and Simpson, M., (2000) "Blood Substitutes," Transfusion Medicine Update, The Institute for Transfusion Medicine.

Kasper, S.M., Grune, F., Walter, M., Amr, N., Erasmi, H., Busello, W., (1998) "The effects of increased doses of bovine hemoglobin on hemodynamics and oxygen transport in patients undergoing preoperative hemodilution for elective abdominal aortic surgery," Anesth. Analg. 87: 284-91.

Koenigsberg, D., Sloan, E., "The efficacy trial of diaspirin cross-linked hemoglobin in the treatment of severe traumatic hemorrhagic shock," (1999) Acad. Emerg. Med. 6: 379-80.

Stowell, C., Levin, J., Spiess, B., Winslow, R., "Progress in the development of RBC substitutes," (2001) Transfusion 41:287-299.

Chang, T., "Modified hemoglobin-based blood substitutes: cross linked, recombinant and encapsulated hemoglobin," (1998) Artificial Cell, 74 Suppl 2:233-41.

Antipov, A., Sukhorukov, G.B., Donath, E., and Möhwald, H., "Sustained Release Properties of Polyelectrolyte Multi-layer Capsules," (2001) J. Phys.Chem. B, 105:2281-2284.

Freemantle, M., "Polyelectrolyte multilayers," (2002) Chem. Eng. News, 80: 44-48.

Ramachandran, G.N., Saisekharan, V., "Conformation of Polypeptides and Proteins," (1968) Adv. Protein Chemistry, 23:283.

Kabanov, V., Zezin, A., "Soluble Interpolymeric Complexes as a New Class of Synthetic Polyelectrolytes," (1984) Pure Appl. Chem. 56:343.

Kabanov, V., "Physicochemical Basis and the Prospects of Using Soluble Interpolyelectrolyte Complexes (Review)," (1994) Polym. Sci., 36:143.

Lvov, Y., Decher, G., "Assembly of Multilayer Ordered Films by Alternating Adsorption of Oppositely Charged Macromolecules," (1994) Crystallog. Rep., 39:628.

Schmitt, J., Grunewald, T., Decher, G., Pershan, P., Kjaer, K., Losche, M., "Internal Structure of Layer-by-Layer Adsorbed Polyelectrolyte Films: A Neutron and X-ray Reflectivity Study," (1993) Macromolecules 26:7058.

Komeev, D., Lvov, Y., Decher, G., Schmitt, J., Yaradaikin, S., "Neutron reflecticity analysis of self-assembled film superlattices with alternate layers of deuterated and hydrogenated polysterenesulfonate and polyallylamine," (1995) Physica B, 213&214:954-956.

Ai, Hua, Jones, Stepven A., deVilliers, Melgardt M., Lvov, Yuri M., "Nano-encapsulation of furosemide microcrystals for controlled drug release," Journal of Controlled Release 86 (2003) 59-68.

http://www.chem.fsu.edu/multilayers/ "Polyelectrolyte Multilayers Home Page,", 2006.

* cited by examiner

MULTILAYER FILMS, COATINGS, AND MICROCAPSULES COMPRISING POLYPEPTIDES

CROSS-REFERENCE TO RELATED APPLICATION

This application is a Continuation-In-Part of U.S. Nonprovisional application Ser. No. 10/652,364 filed Aug. 29, 2003, now U.S. Pat. No. 7,348,399 and also claims the benefit of U.S. 60/729,828 filed Oct. 25, 2005, which are incorporated by reference herein.

BACKGROUND OF THE INVENTION

1. Field of the Invention

The present invention relates to the fabrication of ultrathin multilayered films on suitable surfaces by electrostatic layer-by-layer self assembly ("ELBL"). More specifically, the present invention relates to a method for designing polypeptides for the nanofabrication of thin films, coatings, and microcapsules by ELBL for applications in biomedicine and other fields.

2. Description of Related Art

ELBL is an established technique in which ultrathin films are assembled by alternating the adsorption of oppositely-charged polyelectrolytes. The process is based on the reversal of the surface charge of the film after the deposition of each layer. FIG. 1 shows a schematic diagram of the general ELBL process: films of oppositely charged polyions (cationic polyions 10 and anionic polyions 11) are assembled in successive layers on a negatively-charged planar surface 12; the surface charge is reversed after the deposition of each layer. This process is repeated until a film of desired thickness is formed. The physical basis of association is electrostatics—gravitation and nuclear forces play effectively no role—and the increase in entropy on release of counterions into solution. Because of the generality and relative simplicity of the process, ELBL allows for the deposition of many different types of materials onto many different types of surface. There are, therefore, a vast number of possible useful combinations of materials and surfaces. For a general discussion of ELBL, including its history, see Yuri Lvov, "Electrostatic Layer-by-Layer Assembly of Proteins and Polyions" in *Protein Architecture: Interfacial Molecular Assembly and Immobilization Biotechnology*, Y. Lvov & H. Möhwald eds. (New York: Marcel Dekker, 1999), pp. 125-167, which is incorporated herein by reference in its entirety.

ELBL has recently become a focus area in the field of nanotechnology because it can be used to fabricate films substantially less than 1 micron in thickness. Moreover, ELBL permits exceptional control over the film fabrication process, enabling the use of nanoscale materials and permitting nanoscale structural modifications. Because each layer has a thickness on the order of a few nanometers or less, depending on the type of material used and the specific adsorption process, multilayer assemblies of precisely repeatable thickness can be formed.

A number of synthetic polyelectrolytes have been employed in ELBL applications, including sodium poly(styrene sulfonate) ("PSS"), poly(allylamine hydrochloride) ("PAH"), poly(diallyldimethylammonium chloride) ("PDDA"), poly(acrylamide-co-diallyldimethylammonium chloride), poly(ethyleneimine) ("PEI"), poly(acrylic acid) ("PAA"), poly(anetholesulfonic acid), poly(vinyl sulfate) ("PVS"), and poly(vinylsulfonic acid). Such materials, however, are not generally useful for biomedical applications because they are antigenic or toxic.

Proteins, being polymers with side chains having ionizable groups, can be used in ELBL for various applications, including biomedical ones. Examples of proteins that have been used in ELBL include cytochrome c, hen egg white lysozyme, immunoglobulin G, myoglobin, hemoglobin, and serum albumin (ibid.). There are, however, difficulties with using proteins for this purpose. These include limited control over multilayer structure (because the surface of the protein is highly irregular and proteins will not ordinarily adsorb on a surface in a regular pattern), restrictions on pH due to the pH-dependence of protein solubility and structural stability, lack of biocompatibility when using exogenous proteins, and the cost of scaling up production if the gene has not been cloned; unless the protein were identical in a readily available source, e.g. a cow, the protein would have to be obtained from the organism in which it was intended for use, making the cost of large-scale production of the protein prohibitive.

By contrast polypeptides, which are generally smaller and less complex than proteins, constitute an excellent class of material for ELBL assembly, and polypeptide film structures formed by ELBL will be useful in a broad range of applications. The present invention provides a method for designing polypeptides for the nanofabrication of thin films, coatings, and microcapsules by ELBL. Polypeptides designed using the method of the present invention should exhibit several useful properties, including, without limitation, completely determined primary structure, minimal secondary structure in aqueous solution, monodispersity, completely controlled net charge per unit length, ability to form cross-links on demand, ability to reverse cross-link formation, ability to form more organized thin films than is possible with proteins, and relatively inexpensive large-scale production cost (assuming gene design, synthesis, cloning, and host expression in *E. coli* or yeast, or peptide synthesis).

Polypeptides designed using the method of the present invention have been shown useful for ELBL of thin film structures with targeted or possible applications in biomedical technology, food technology, and environmental technology. Such polypeptides could be used, for example, to fabricate artificial red blood cells, drug delivery devices, and antimicrobial films.

BRIEF SUMMARY OF THE INVENTION

In one embodiment, a multilayer film comprises two or more layers of polyelectrolytes, wherein adjacent layers comprise oppositely charged polyelectrolytes. A first layer polypeptide comprises one r more first amino acid sequence motifs, wherein the one or more first amino acid sequence motifs has a length of 5 to 15 amino acids residues, and wherein the balance of charge in the first amino acid sequence motif at pH 7 is greater than or equal to approximately one-half of the length of the first amino acid sequence motif. The first layer polypeptide is not a homopolymer, is at least 15 amino acid residues long, and has a balance of charge at pH 7 greater than or equal to approximately one-half of the total length of the first layer polypeptide. Further, a second layer comprises second layer polyelectrolyte comprising a nonprotein polyelectrolyte having a charge opposite that of the first layer polypeptide.

The present invention also provides a novel method for identifying "sequence motifs" of a defined length and net charge at neutral pH in amino acid sequence information for use in ELBL, and recording a desired number of the motifs.

The method comprises the steps of: (a) Obtaining an amino acid sequence for a peptide or a protein from a particular organism; (b) Locating a starter amino acid in the amino acid sequence; (c) Examining the starter amino acid and the following n amino acids to determine the number of charged amino acids having a polarity opposite the certain polarity; (d) If the number of the charged amino acids having a polarity opposite the certain polarity is one or more, continuing the method at step g; (e) Examining the starter amino acid and the following n amino acids to determine the number of charged amino acids having the certain polarity; (f) If the number of charged amino acids having the certain polarity is equal to or greater than x, recording the amino acid sequence motif consisting of the starter amino acid and the following n amino acids; (g) Locating another starter amino acid in the amino acid sequence; and (h) Repeating the method beginning at step c until the desired number of amino acid sequence motifs have been identified or all of the amino acids in the amino acid sequence have been used as the starter amino acid in step c; wherein x is greater than or equal to approximately one-half of n.

The present invention also provides a novel method for designing a polypeptide for use in ELBL, comprising the steps of: (a) Identifying and recording one or more amino acid sequence motifs having a net charge of a certain polarity using the steps mentioned in the preceding paragraph and (b) Joining a plurality of said recorded amino acid sequence motifs to form a polypeptide.

The present invention also provides a novel method for designing a polypeptide for use in ELBL comprising the following steps: (a) Designing de novo a plurality of amino acid sequence motifs, wherein said amino acid sequence motifs consist of n amino acids, at least x of which are positively charged and none is negatively charged, or at least x of which are negatively charged and none is positively charged, wherein x is greater than or equal to approximately one-half of n; and (b) Joining said plurality of said amino acid sequence motifs. The amino acid sequence motifs can comprise the 20 usual amino acids or non-natural amino acids, and the amino acids can be either left-handed (L-amino acids) or right handed (D-amino acids).

The present invention also provides a thin film, the film comprising a plurality of layers of polypeptides, the layers of polypeptides having alternating charges, wherein the polypeptides comprise at least one amino acid sequence motif consisting of n amino acids, at least x of which are positively charged and none is negatively charged, or at least x of which are negatively charged and none is positively charged, wherein x is greater than or equal to approximately one-half of n. The motifs in these polypeptides may be selected using either of the methods described above.

The present invention also provides a novel process for using cysteine and other sulphydryl-containing amino acid types to "lock" and "unlock" the layers of polypeptide ELBL films. This process enables the films to remain stable at extremes of pH, giving greater control over the mechanical stability and diffusive properties of films nanofabricated from designed polypeptides and increasing their utility in a broad range of applications.

DETAILED DESCRIPTION OF THE INVENTION

Explanations of Terms

Figure 1:
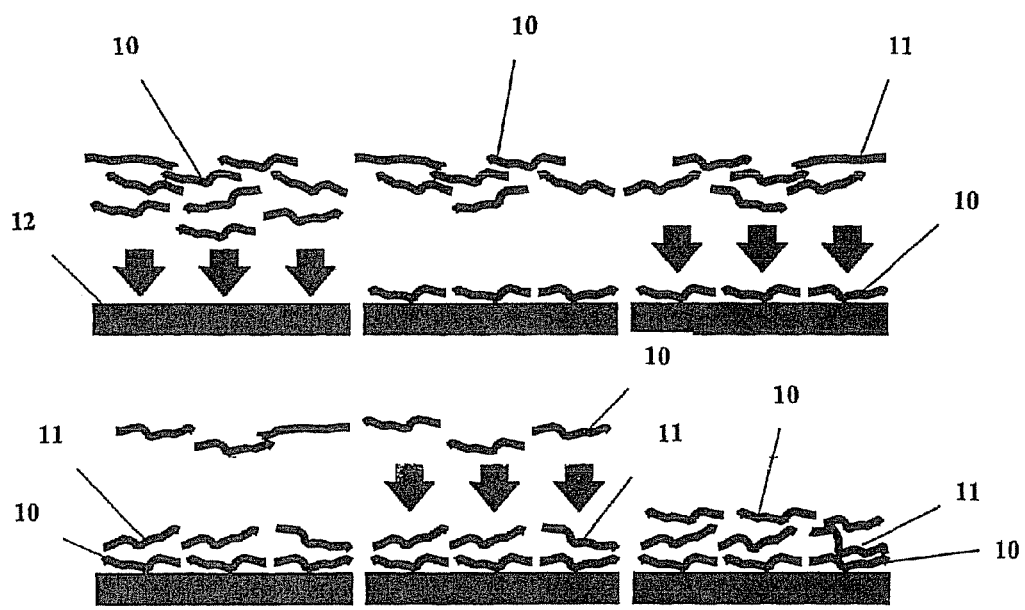
FIG. 1 is a schematic diagram of the general ELBL process.

For convenience in the ensuing description, the following explanations of terms are adopted. However, these explanations are intended to be exemplary only. They are not intended to limit the terms as they are described or referred to throughout the specification. Rather, these explanations are meant to include any additional aspects and/or examples of the terms as described and claimed herein.

As used herein, "layer" means a thickness increment, e.g., on a template for film formation, following an adsorption step. "Multilayer" means multiple (i.e., two or more) thickness increments. A "polyelectrolyte multilayer film" is a film comprising one or more thickness increments of polyelectrolytes. After deposition, the layers of a multilayer film may not remain as discrete layers. In fact, it is possible that there is significant intermingling of species, particularly at the interfaces of the thickness increments.

As used herein, "biocompatibility" means causing no adverse health effect upon ingestion, contact with the skin, or introduction to the bloodstream.

As used herein, "immune response" means the response of the human immune system to the presence of a substance in the bloodstream. An immune response can be characterized in a number of ways, for example, by an increase in the bloodstream of the number of antibodies that recognize a certain antigen. (Antibodies are proteins made by the immune system, and an antigen is an entity that generates an immune response.) The human body fights infection and inhibits reinfection by increasing the number of antibodies in the bloodstream. The specific immune response depends somewhat on the individual, though general patterns of response are the norm.

As used herein, "epitope" means the structure of a protein that is recognized by an antibody. Ordinarily an epitope will be on the surface of a protein. A "continuous epitope" is one that involves several amino acids in a row, not one that involves amino acid residues that happen to be in contact in a folded protein.

As used herein, "sequence motif" and "motif" mean a contiguous amino acid sequence of a given number of residues identified using the method of the current invention. In a preferred embodiment, the number of residues is 7.

As used herein, "amino acid sequence" and "sequence" mean any length of polypeptide chain that is at least two amino residues long.

As used herein, "residue" means an amino acid in a polymer; it is the residue of the amino acid monomer from which the polymer was formed. Polypeptide synthesis involves dehydration, that is, a single water molecule is "lost" on addition of the amino acid to a polypeptide chain.

As used herein, "designed polypeptide" means a polypeptide designed using the method of the present invention, and the terms "peptide" and "polypeptide" are used interchangeably.

As used herein, "primary structure" means the linear sequence of amino acids in a polypeptide chain, and "secondary structure" means the more or less regular types of structure stabilized by non-covalent interactions, usually hydrogen bonds—examples include α-helix, β-sheet, and β-turn.

As used herein, "amino acid" is not limited to the 20 naturally occurring amino acids; the term also refers to D-amino acids, L-amino acids, and non-natural amino acids, as the context permits.

As used herein, "non-natural amino acids" means amino acids other than the 20 naturally occurring ones.

A "peptoid," or N-substituted glycine, means an analog of the corresponding amino acid monomer, with the same side chain as the corresponding amino acid but with the side chain appended to the nitrogen atom of the amino group rather than to the α-carbons of the residue. Consequently, the chemical linkages between monomers in a polypeptoid are not peptide bonds, which can be useful for limiting proteolytic digestion.

"Substrate" means a solid material with a suitable surface for adsorption of polyelectrolytes from aqueous solution. The surface of a substrate can have essentially any shape, for example, planar, spherical, rod-shaped, etc. A substrate surface can be regular or irregular. A substrate can be a crystal. Substrates range in size from the nanoscale to the macroscale. Moreover, a substrate optionally comprises a collection of colloidal particles. A substrate can be made of organic material, inorganic material, bioactive material, or a combination thereof. Nonlimiting examples of substrates silicon wafers; charged colloidal particles, e.g., microparticles of $CaCO_3$ or of melamine formaldehyde; biological cells such as erythrocytes, hepatocytes, bacterial cells, or yeast cells; organic polymer lattices, e.g., polystyrene or styrene copolymer lattices; liposomes; organelles; and viruses. In one embodiment, a substrate is a medical device such as an artificial pacemaker, a cochlear implant, or a stent.

When a substrate is disintegrated or otherwise removed during or after film formation, it is called "a template" (for film formation). Template particles can be dissolved in appropriate solvents or removed by thermal treatment. If, for example, partially cross-linked melamine-formaldehyde template particles are used, the template can be disintegrated by mild chemical methods, e.g., in dimethylsulfoxide (DMSO), or by a change in pH value. After dissolution of the template particles, hollow multilayer shells remain which are composed of alternating polyelectrolyte layers.

A "microcapsule" is a polyelectrolyte film in the form of a hollow micro-scale shell or a coating surrounding a core. The core can comprise a variety of different encapsulants, for example, a protein, a drug, or a combination thereof.

"Bioactive molecule" means a molecule, macromolecule or a macromolecular assembly having a biological effect. The specific biological effect can be measured in a suitable assay for measuring the biological effect and normalizing per unit weight or per molecule of the bioactive molecule. A bioactive molecule can be encapsulated or retained behind a polypeptide film. Nonlimiting examples of a bioactive molecule are a protein, a functional fragment of a protein, a complex of proteins, an oligopeptide, an oligonucleotide, a nucleic acid, a ribosome, an active therapeutic agent, a phospholipid, a polysaccharide, a functional membrane fragment, a membrane structure, a virus, a pathogen, a cell, an aggregate of cells, and an organelle. Examples of a protein that can be encapsulated or retained within a polypeptide film are hemoglobin; enzymes, such as for example glucose oxidase, urease, lysozyme and the like; extracellular matrix proteins, such as for example fibronectin, laminin, vitronectin and collagen; and an antibody. Examples of a cell that can be encapsulated or retained within a polypeptide film is a transplanted islet cell, a eukaryotic cell, a bacterial cell, a plant cell, and a yeast.

The following three-letter abbreviations are used herein for the 20 usual amino acids:

Ala = alanine
Glu = glutamic acid
His = histidine
Leu = leucine
Pro = proline
Ser = serine
Trp = tryptophan
Cys = cysteine
Phe = phenylalanine
Ile = isoleucine
Met = methionine
Gln = glutamine
Thr = threonine
Tyr = tyrosine
Asp = aspartic acid
Gly = glycine
Lys = lysine
Asn = asparagine
Arg = arginine
Val = valine A. Description of the Invention The present invention includes multilayer films comprising alternating layers of oppositely charged polyelectrolytes, wherein a first layer of the films comprises a designed polypeptide. "Designed polypeptide" means a polypeptide comprising one or more amino acid sequence motifs, wherein the polypeptide is not a homopolymer, is at least 15 amino acid residues long, and has a balance of charge at pH 7 greater than or equal to approximately one-half of the total length of the first layer polypeptide.

A second layer polylectrolyte has a charge opposite that of the first layer polypeptide and comprises a nonpeptide polylelectrolyte. Suitable nonprotein polyelectrolytes include, for example, hyaluronate, alginate, poly(styrene sulfonate) ("PSS"), poly(allylamine hydrochloride) ("PAH"), poly(diallyldimethylammonium chloride) ("PDDA"), poly(acrylic acid) ("PAA"), poly(vinyl sulfate) ("PVS"), nucleic acids, or a combination comprising one or more of the foregoing polyelectrolytes.

The present invention also provides a method for designing polypeptides for the nanofabrication by ELBL of thin films, coatings, and microcapsules for applications in biomedicine and other fields. The method involves 5 primary design concerns: (1) the electrostatic properties of the polypeptides; (2) the physical structure of the polypeptides; (3) the physical stability of the films formed from the polypeptides; (4) the biocompatibility of the polypeptides and films; and (5) the bioactivity of the polypeptides and films. The first design concern, electrostatics, is perhaps the most important because it is the basis of ELBL. Without suitable charge properties, a polypeptide will not be soluble in aqueous solution and cannot be used for the ELBL nanofabrication of films. We have devised a novel process for identifying in amino acid sequence information amino acid sequence motifs having electrostatic properties suitable for ELBL.

Figure 11A:
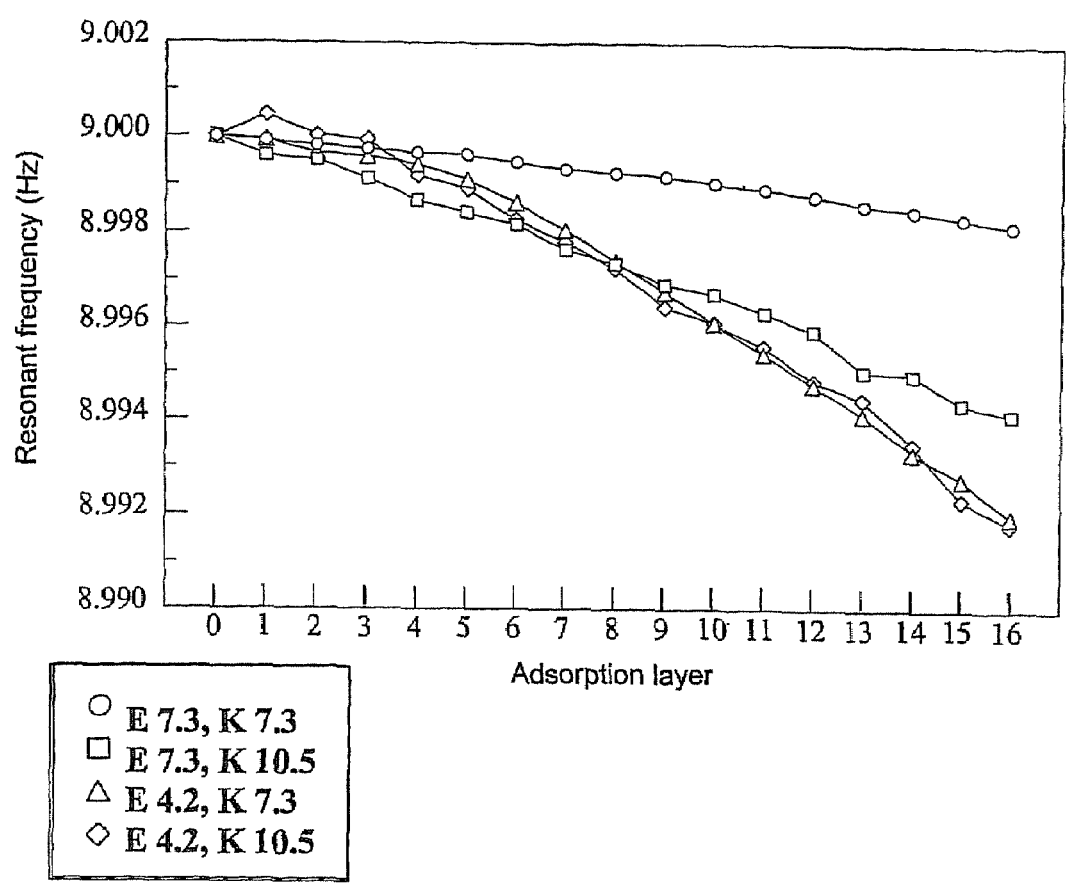
FIG. 11(a) illustrates the role of solution structure of peptides on film assembly, showing how the assembly behavior of poly-L-glutamate and poly-L-lysine depends on pH. QCM resonant frequency is plotted against adsorption layer. The average molecular mass of poly-L-glutamate was 84,600 Da, while that of poly-L-lysine was 84,000 Da. The numbers refer to pH values. E=Glu, K=Lys. The peptide concentration used for assembly was 2 mg/mL.
Figure 11B:
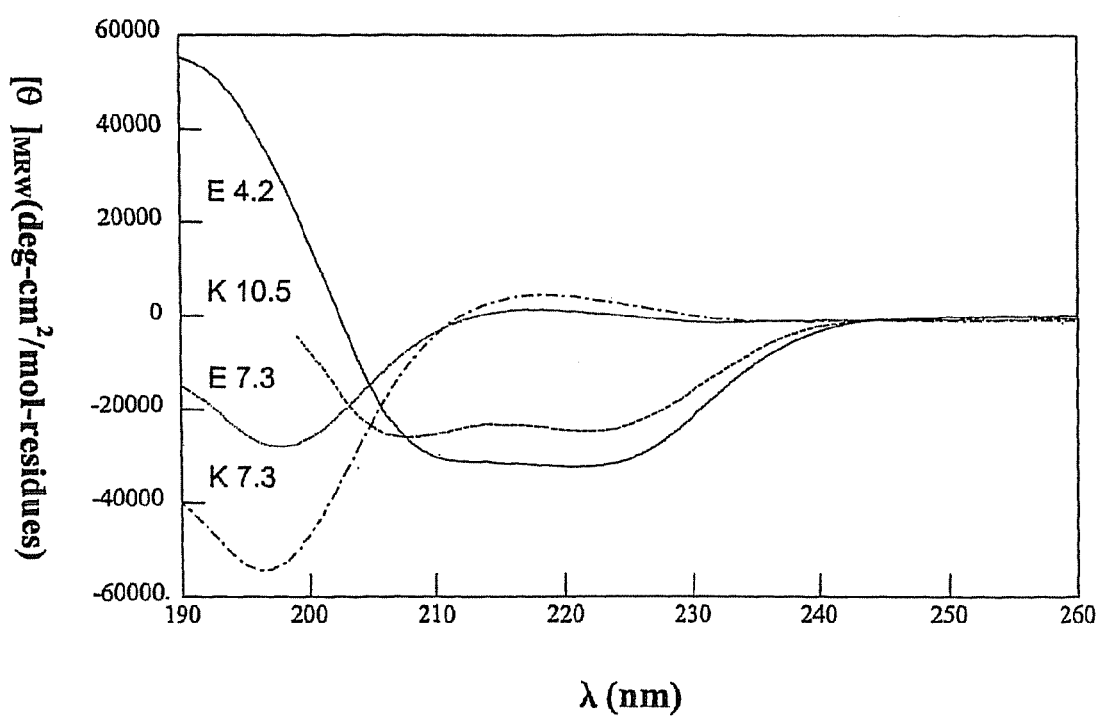
FIG. 11(b) illustrates the role of solution structure of peptides on film assembly, showing how the solution structure of poly-L-glutamate and poly-L-lysine depends on pH. Mean molar residue ellipticity is plotted as a function of pH. The peptide concentration was 0.05 mg/mL.

The secondary structure of the polypeptides used for ELBL is also important, because the physical properties of the film, including its stability, will depend on how the solution structure of the peptide translates into its structure in the film. FIG. 11 illustrates how the solution structure of certain polypeptides correlates with film assembly. Panel (a) shows how the assembly behavior of poly-L-glutamate and poly-L-lysine depends on pH. It is clear that the α-helix conformation correlates with a greater extent of deposited material than the β-sheet conformation. The precise molecular interpretation of this behavior remains to be elucidated. Panel (b) shows how the solution structure of these peptides depends on pH. At pH 4.2 poly-L-glutamate is largely α-helical, as is poly-L-lysine at pH 10.5. Both polypeptides are in a largely unstructured coil-like conformation at pH 7.3.

The remaining concerns relate to the applications of the polypeptide films. In practicing the invention, more or less weight will be placed on these other concerns depending on the design requirements of a particular application.

By using the selection process of the present invention to identify in amino acid sequence information amino acid sequence motifs having suitable charge characteristics, and using the other design concerns to select particular motifs, one can design polypeptides suitable for the ELBL fabrication of nano-organized films for applications in biomedicine and other fields. Alternatively, one can use the method of the present invention to design polypeptides de novo for use in ELBL. The approach to de novo design is essentially the same as identifying motifs in existing amino acid sequence information, except that each residue in an amino acid sequence motif is selected by the practitioner rather than an entire motif being identified in the genomic or proteomic information of a specific organism. It must be emphasized that the fundamental polypeptide design principles adduced in the present invention are independent of whether the amino acids involved are the 20 naturally-occurring ones, non-natural amino acids, or some novel combination of these, in the case of de novo polypeptide design. Further, both D-amino acids and L-amino acids could be used.

The design concerns of the present invention are discussed in more detail below.

1. Electrostatics

We have devised a novel process for identifying in amino acid sequence information amino acid sequence motifs having electrostatic properties suitable for ELBL. Using this process, we have identified 88,315 non-redundant amino acid sequence motifs in human proteome data—the translation of the portion of the genome that encodes all known proteins in the human body. This information is available at the National Center for Biotechnology Information's ("NCBI") Web site, among other places. Such information is constantly being updated as the human genome is further analyzed. As the amount of such information increases, the number of amino acid sequence motifs that could be identified in human sequence information by the selection process of the present invention as having suitable electrostatic properties for ELBL will also increase. The same is true for any organism. Accepted biochemical and physics principles, as well as the experimental results described below, indicate that the identified sequence motifs will be useful for the design of polypeptides for the nanofabrication of ELBL structures.

The key selection criterion is the average charge per unit length at neutral pH (pH 7, close to the pH of human blood). In addition, there are several structural preferences. First, it is preferred that each amino acid sequence motif consist of only 7 residues.

a. Total Number of Residues in the Motif

In one exemplary embodiment, a motif length of 7 was chosen in an effort to optimize biocompatibility, physical structure, and the number of non-redundant sequence motifs in available amino acid sequence data.

In one embodiment, at least half of the amino acid residues in each sequence motif is charged, such that the net charge on the amino acid sequence motif per residue is greater than or equal to 0.5. Moreover, it is preferred, but not required, that all of the charged residues in each motif be of the same sign of charge. These requirements ensure that each motif will be sufficiently soluble in aqueous solvent and have sufficient charge at neutral pH to be useful for ELBL. Because only a relatively small percentage of amino acid types are charged, as the length of a given amino acid sequence increases, the odds decrease that the sequence will have a sufficient percentage of appropriately charged amino acids for ELBL. 4 charged amino acids is the preferred minimum for a motif size of 7, because fewer than 4 charges yields substantially decreased peptide solubility and decreased control over ELBL.

Regarding biocompatibility (discussed further below), each identified sequence motif is long enough at 7 residues to constitute a continuous epitope (relevant to the possible immune response of an organism into which a designed peptide might be introduced), but not so long as to correspond substantially to residues both on the surface of a protein and in its interior; the charge requirements help to ensure that the sequence motif occurs on the surface of the folded protein; a charged residue cannot be formed in the core of a folded protein. By contrast, a very short motif could appear to the body to be a random sequence, or one not specifically "self," and therefore elicit an immune response. Although the ideal length of a peptide for generating antibodies is a point of some dispute, most peptide antigens range in length from 12 to 16 residues. Motifs that are 9 residues or shorter can be effective antigens; peptides longer than 12 to 16 amino acids may contain multiple epitopes (Angeletti, R. H. (1999) Design of Useful Peptide Antigens, *J. Biomol. Tech.* 10:2-10, which is hereby incorporated by reference in its entirety). Thus, to minimize antigenicity one would prefer a motif shorter than 12 and, better yet, shorter than 9 residues.

Figure 2:
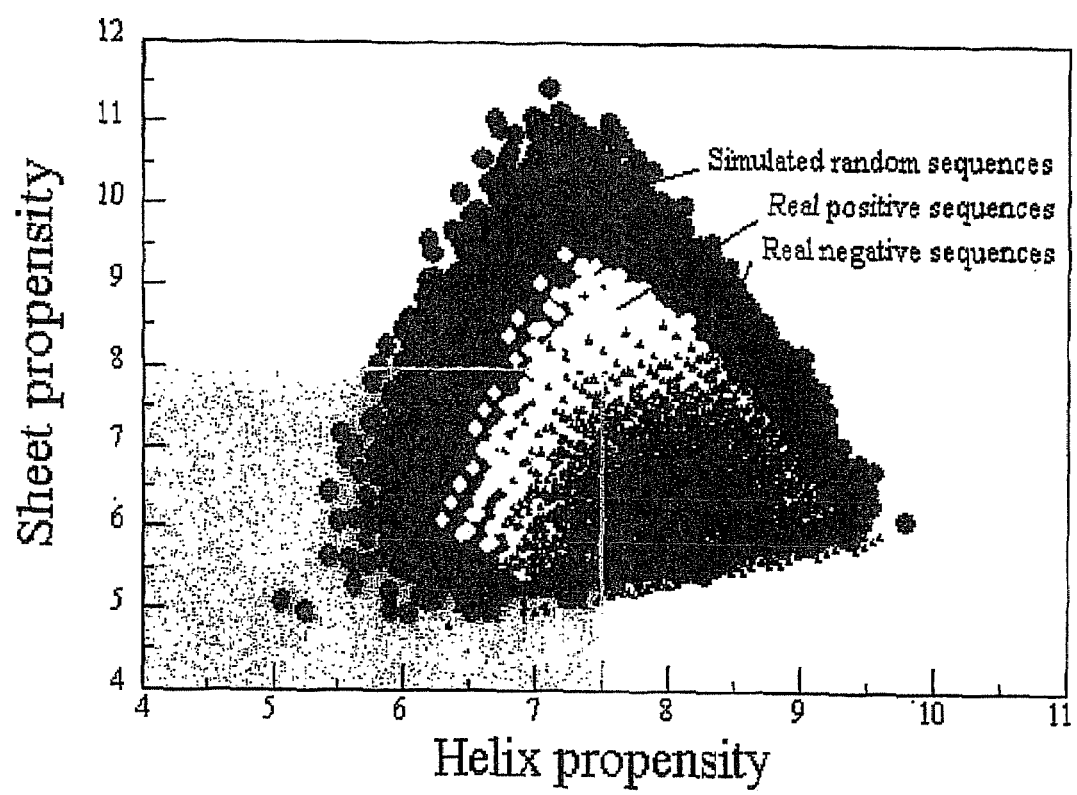
FIG. 2 is a graph of the cumulative secondary structure propensities of the amino acid sequence motifs identified in human amino acid sequence information using the method of the present invention, compared with the distribution of structure propensities of $10^5$ random amino acid sequences.

The preferred motifs should not be too long for another reason: to minimize secondary structure formation. Secondary structure decreases control of the physical structure of the polypeptides (see below) and the films made from them. Thus, an amino acid sequence motif should contain 5 to 15 contiguous amino acids.

Furthermore, the maximum number of non-redundant motifs in the human genome is found when the number of residues in each motif is 7. FIG. 6 shows the number of non-redundant sequence motifs in available human amino acid sequence information. The greatest number of positive motifs is for a 5-residue length, while the greatest number of negative motifs is for a 7-residue length. The greatest number of positive and negative motifs is about the same for 5 and 7. Thus, a motif length of 7 residues would appear to maximize the number of non-redundant motifs.

For all of the above reasons, 7 residues is the preferred length of motif to optimize polypeptide design for ELBL. Nevertheless, it is possible that in some cases either slightly shorter or slightly longer motifs will work equally as well. For example, motifs 5 or 6 residues long may be employed, and motifs on the order of 8 to 15 residues in length could also be useful. Thus, an amino acid sequence motif is defined as having 5 to 15 amino acid residues.

b. Number of Charged Residues

Second, it is preferred that at least 4 positively-charged (basic) amino acids (Arg, His, or Lys) or at least 4 negatively-charged (acidic) amino acids (Glu or Asp) are present in each 7-residue motif at neutral pH. Combinations of positive and negative charges are disfavored in an effort to ensure a sufficiently high charge density at neutral pH. It is possible, however, that a motif containing both positive and negative amino acids could be useful for ELBL. For example, a slightly longer motif, say of 9 residues, could have 6 positively charged amino acids and 1 negatively charged amino acid. It is the balance of charge (i.e., the net charge) that is important—the overall peptide must be either sufficiently positively charged or sufficiently negatively charged at neutral pH. Preferred embodiments of the motifs, however, will contain only Glu or Asp or only Arg, His, or Lys as the charged amino acids (although other non-charged amino acids could, and ordinarily do, form part of the motifs), unless non-natural amino acids are admitted as acidic or basic amino acids.

FIG. 5 is a flow chart showing the steps involved in an exemplary selection process for identifying amino acid sequences having suitable electrostatic properties. It is assumed that only the 20 usual amino acids are involved. If searching for negatively-charged motifs, the process begins by locating an amino acid in the sequence data. This amino acid will be called the "starter amino acid" because it is the starting point for the analysis of the surrounding amino acids (i.e., it will begin the motif). Next, the starter amino acid and the following 6 residues are examined for occurrences of Arg, His, or Lys. If one or more Arg, His, or Lys is located in these 7 amino acids, the process is begun anew at another starter amino acid. If no Arg, His, or Lys is found, the 7 amino acids are examined to determine the number of occurrences of Glu and/or Asp. If there are at least 4 occurrences of Glu and/or Asp in the 7 residues, the sequence motif is cataloged. The selection process is essentially the same for positively charged amino acids, except that Glu and Asp are replaced by Arg, His, and Lys, and Arg, His, and Lys are replaced by Glu and Asp, respectively. Obviously, one could also begin the method at the beginning of the amino acid sequence (amino terminus) and proceed to the end (carboxyl terminus), or, alternatively, one could begin at a random point and work through all of the amino acids in the sequence, randomly or systematically in either direction. Moreover, one could use the method to identify motifs in sequence information containing non-natural amino acids. In such a case, one would search for non-natural acidic or basic amino acids instead of Glu and Asp, and Arg, Lys, and His, respectively.

In one embodiment, the one or more first amino acid sequence motifs consists of n amino acids, wherein the balance of charge in the first amino acid sequence motif at pH 7 is greater than or equal to approximately one-half of n, and wherein n is 5 to 15.

The remaining design concerns, namely, physical structure, physical stability, biocompatibility, and biofunctionality, deal primarily with the particular application for which the designed polypeptides will be used. As noted above, more or less weight will be placed on these concerns during the design process, depending on the desired peptide properties for a particular application.

2. Physical Structure

A design concern regarding the amino acid sequence motifs is their propensity to form secondary structures, notably α-helix or β-sheet. We have sought in several ways to control, notably minimize, secondary structure formation of designed polypeptides in an aqueous medium in order to maximize control over thin film layer formation. First, it is preferred that the sequence motifs be relatively short, because long motifs are more likely to adopt a stable three-dimensional structure in solution. Second, we place a glycine residue between each motif in preferred embodiments of the polypeptide designs. Glycine has a very low α-helix propensity and a very low β-sheet propensity, making it energetically very unfavorable for a glycine and its neighboring amino acids to form regular secondary structure in aqueous solution. Proline has similar properties in some respects and could be used as an alternative to glycine to join motifs. Third, we have sought to minimize the α-helix and β-sheet propensity of the designed polypeptides themselves by focusing on motifs for which the summed a-helix propensity is less than 7.5 and the summed β-sheet propensity is less than 8. ("Summed" propensity means the sum of the a-helix or β-sheet propensities of all amino acids in a motif.) It is possible, however, that amino acid sequences having a somewhat higher summed α-helix propensity and/or summed β-sheet propensity would be suitable for ELBL under some circumstances, as the Gly (or Pro) residues between motifs will play a key role in inhibiting stable secondary structure formation in the designed polypeptide. In fact, it may be desirable in certain applications for the propensity of a polypeptide to form secondary structure to be relatively high, as a specific design feature of thin film fabrication; the necessary electrostatic charge requirements for ELBL must still be met, as discussed above.

In order to be able to select amino acid sequences with desired secondary structure propensities, we first calculated the secondary structure propensities for all 20 amino acids using the method of Chou and Fasman (see P. Chou and G. Fasman *Biochemistry* 13:211 (1974), which is incorporated by reference herein in its entirety) using structural information from more than 1,800 high-resolution X-ray crystallographic structures (1,334 containing α-helices and 1,221 containing β-strands). Structures were selected from the Protein Data Bank (a publicly-accessible repository of protein structures) based on: (a) method of structure determination (X-ray diffraction); (b) resolution (better than 2.0 Å)—"resolution" in this context refers to the minimum size of a structure one can resolve, as in the Rayleigh criterion; and (c) structural diversity (less than 50% sequence identity between the protein crystallographic structures used to compute the helix and sheet propensities of the various amino acids). The rationale was to choose high resolution structures determined by the most reliable methodology and not to bias the propensity calculation by having similar structures. Next, for comparison 100,000 non-redundant random sequences were produced using a random number generator in a personal computer. We then calculated the secondary structure propensities for the 88,315 amino acid sequences identified using the selection process described in part VII(B)(1) above (59,385 non-redundant basic sequence motifs and 28,930 non-redundant acidic sequence motifs). The propensities for the random sequences were then compared to the propensities of the selected sequences. FIG. 2 shows the distribution of secondary structure formation propensities in these sequence motifs. The rectangle in FIG. 2 highlights the sequence motifs we have identified as least likely to form secondary structure on the basis of secondary structure propensities.

3. Physical Stability

Another design concern is control of the stability of the polypeptide ELBL films. Ionic bonds, hydrogen bonds, van der Waals interactions, and hydrophobic interactions provide some, albeit relatively limited, stability to ELBL films. By contrast, covalent disulfide bonds could provide exceptional structural strength. We have devised a novel process for using cysteine (or some other type of sulfhydryl-containing amino acid) to "lock" and "unlock" adjacent layers of polypeptide ELBL film. This process enables a polypeptide nanofabricated film to remain stable at extremes of pH, giving greater control over its mechanical stability and diffusive properties (for discussions of porosity of multilayer films made of non-polypeptide polyelectrolytes, see Caruso, F., Niikura, K., Furlong, N. and Okahata (1997) *Langmuir* 13:3427 and Caruso, F., Furlong, N., Ariga, K., Ichinose, I., and Kunitake, T. (1998) *Langmuir* 14:4559, both of which are incorporated herein by reference in their entireties). Also, the incorporation of cysteine (or some other type of sulfhydryl-containing amino acid) in a sequence motif of a designed polypeptide enables the use of relatively short peptides in thin film fabrication, by virtue of intermolecular disulfide bond formation. Without cysteine, such peptides would not generally yield sufficiently stable films (see FIG. 12, discussed below). Thus, our novel use of cysteine will obviate the need to produce expensive long versions of the designed polypeptides in a substantial percentage of possible applications. This will be particularly advantageous in situations where the thin film is to be fabricated over material to be encapsulated, for example a small crystal of a drug, a small spherical hemoglobin crystal, or a solution containing hemoglobin.

For applications in which the physical stability of the films is important, amino acid sequence motifs containing cysteine (or some other type of sulfhydryl-containing amino acid) may be selected from the library of motifs identified using the methods discussed above, or designed de novo using the principles described above. Polypeptides can then be designed and fabricated based on the selected or designed amino acid sequence motifs. Once the polypeptides have been synthesized chemically or produced in a host organism, ELBL assembly of cysteine-containing peptides is done in the presence of a reducing agent, to prevent premature disulfide bond formation. Following assembly, the reducing agent is removed and an oxidizing agent is added. In the presence of the oxidizing agent disulfide bonds form between cysteine residues, thereby "locking" together the polypeptide layers that contain them.

This "locking" method may be further illustrated using the following specific example of microcapsule fabrication. First, designed polypeptides containing cysteine are used to form multilayers by ELBL on a suitably charged spherical surface, normally in aqueous solution at neutral pH and in the presence of dithiothreitol ("DTT"), a reducing agent. Next, DTT is removed by filtration, diffusion, or some other similar method known in the art, causing cysteine to form from pairs of cysteine side chains and thereby stabilizing the film. If the peptide multilayers are constructed on a core particle containing the materials one wishes to encapsulate, for instance a crystalline material, the fabrication process is complete and the core particle can thereafter be made to dissolve in the encapsulated environment, for example by a change of pH. If, however, the multilayers are constructed on a "dummy" core particle, the core must be removed. In the case of melamine formaldehyde particles ("MF"), for example, the core is ordinarily dissolved by decreasing the pH—dissolution is acid-catalyzed. Following dissolution of the core, the pH of solution is adjusted to 4, where partial charge on the peptide polyanions makes the microcapsules semi-permeable (compare Lvov et al. (2001) *Nano Letters* 1:125, which is hereby incorporated herein in its entirety). Next, 10 mM DTT is added to the microcapsule solution to reduce cystine to cysteine. The microcapsules may then be "loaded" by transferring them to a concentrated solution of the material to be encapsulated, for example a protein (ibid.). The protein enters the microcapsules by moving down its concentration gradient. The encapsulated protein is "locked in" by removal of reductant and addition of oxidant, thereby promoting the reformation of disulfide bonds.

Figure 4A:
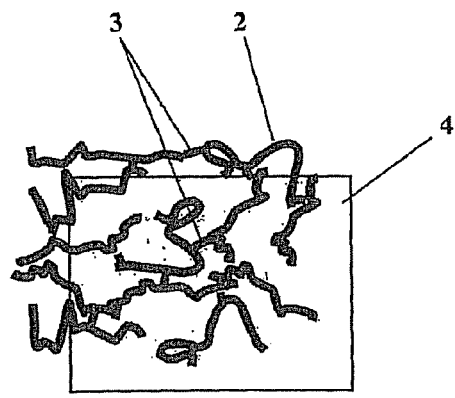
FIG. 4(a) illustrates intra-layer disulfide bonds according to the cysteine locking method of the present invention.
Figure 4B:
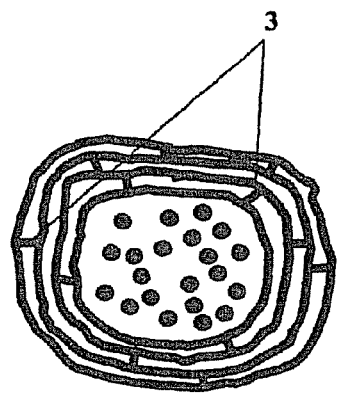
FIG. 4(b) illustrates inter-layer disulfide bonds according to the cysteine locking method of the present invention.
Figure 4C:
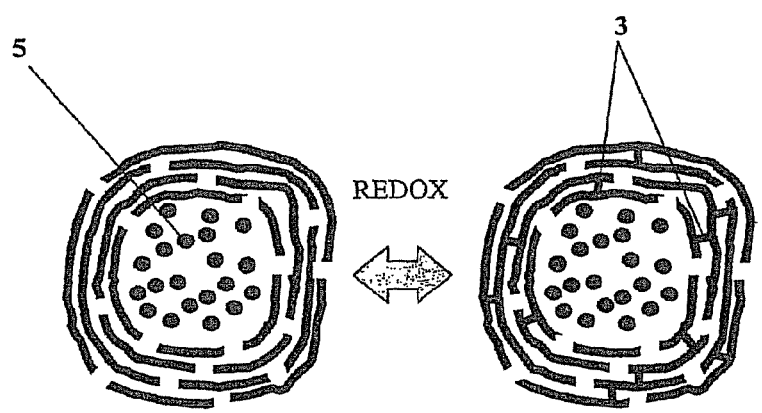
FIG. 4(c) illustrates the oxidation and reduction of disulfide bonds in microcapsules fabricated from polypeptides designed according to the method of the present invention.
Figure 5:
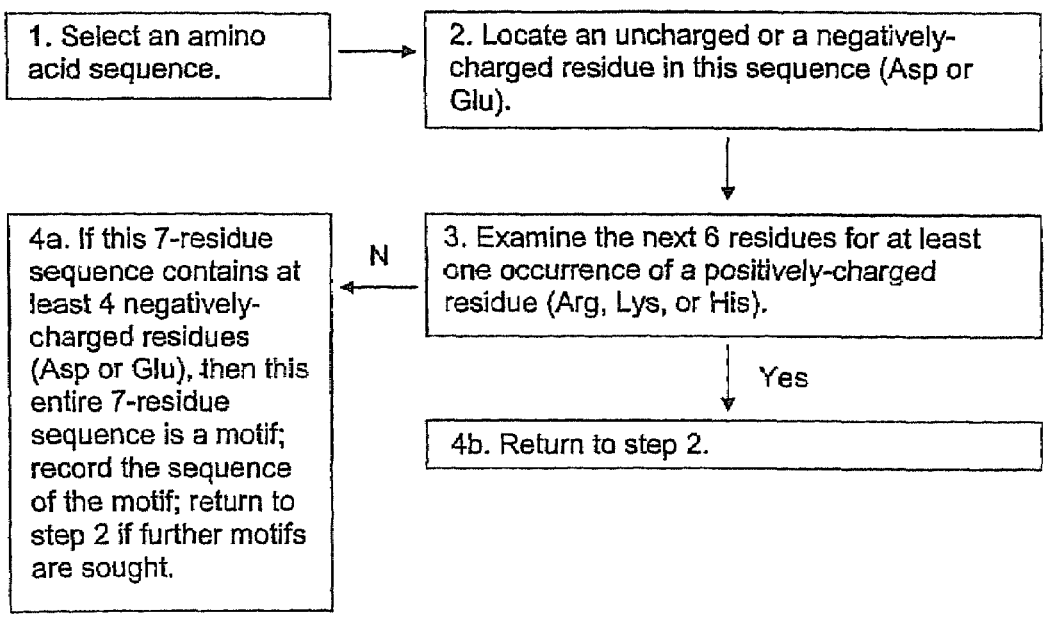
FIG. 5 is a schematic of the selection process of the present invention used to identify in existing amino acid sequence information amino acid sequence motifs having suitable electrostatic properties for ELBL.
Figure 6:
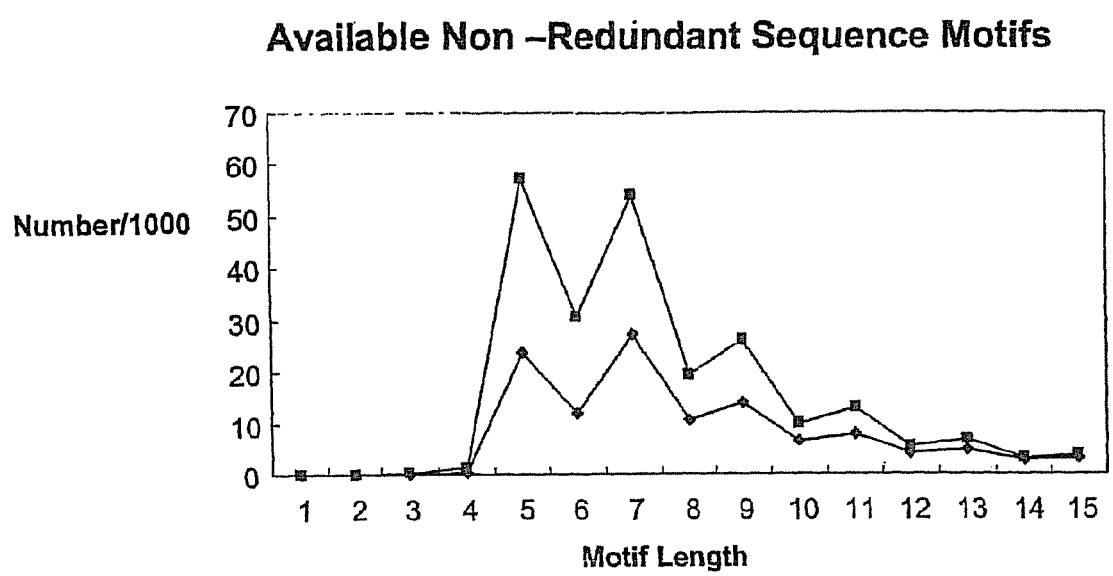
FIG. 6 shows the number of non-redundant sequence motifs identified in available human amino acid sequence data.

A schematic of the cysteine "locking" and "unlocking" method of the present invention is shown in FIG. 4. Cysteine can form both intra- and inter-molecular disulfide bonds. Further, disulfide bonds can be formed between molecules in the same layer or adjacent layers, depending on the location of cysteine-containing peptides in the film. Referring to FIG. 4(a), basic polypeptides 2 are linked by disulfide bonds 3 in all layers in which the basic peptides contain cysteine. The acidic peptides of the intervening layer (represented in the figure by a translucent layer 4) do not contain cysteine. However, alternating layers continue to attract each other electrostatically, if the acidic and basic side chains are charged at the pH of the surrounding environment. Referring to FIG. 4(b), disulfide bonds are shown between layers. Such structures will form when both the acidic and basic polypeptides (i.e., alternating polypeptide layers) used for ELBL contain cysteine and the procedure used has been suitable for disulfide bond formation. Referring to FIG. 4(c), reduction and oxidation reactions are used to regulate the release of encapsulated compounds 5 by breaking and forming disulfide bonds 3, respectively, and thereby regulating the diffusion of particles through the capsule wall.

The cysteine "locking" and "unlocking" is a novel way of regulating the structural integrity and permeability of ELBL films. It is known in the art that glutaraldehyde can be used to cross-link proteins, and this chemical could therefore be used to stabilize polypeptide films. Glutaraldehyde cross-linking, however, is irreversible. In contrast, the cysteine "locking" and "unlocking" method of the present invention is reversible and, therefore, offers better control over structure formation and, importantly, use of the films and capsules that can be fabricated using the present invention. Blood is an oxidizing environment. Thus, in certain biomedical applications, for example artificial red blood cells or drug delivery systems fabricated from designed polypeptides, exposing Cys-crosslinked polypeptide film to the blood or some other oxidizing environment after the formation of disulfide bonds is not expected to cause those bonds to be broken. Finally, it should also be noted that applications involving non-natural amino acids would replace Cys with some other sulfhydryl-containing amino acid type. For example, a sulfhydryl could be added to β-amino acids such as D,L-β-amino-β-cylohexyl propionic acid; D,L-3-aminobutanoic acid; or 5-(methylthio)-3-aminopentanoic acid (see http://www.synthatex.com).

4. Biocompatibility

Biocompatibility is a major design concern in biomedical applications. In such applications, the practitioner of the present invention will aim to identify genomic or proteomic information that will yield "immune inert" polypeptides, particularly if the fabricated or coated object will make contact with circulating blood. For purposes of the present invention, it is preferred that the selection process discussed in Part VII(B)(1) above be used to analyze the amino acid sequences of blood proteins. This will maximize the odds of minimizing the immune response of an organism.

Computer algorithms exist for predicting the antigenicity of an amino acid sequence. Such methods, however, are known in the art to be semi-reliable at best. In the present invention, the sequence motifs identified using the selection method discussed above in Part VII(B)(1) are highly polar. The motifs must, therefore, occur on the surface of the native state of the proteins of which they are part of the sequence. The "surface" is that part of a folded protein that is in contact with the solvent or inaccessible to the solvent solely because of the granular nature of water. The "interior" is that part of a folded protein that is inaccessible to solvent for any other reason. A folded globular soluble protein is like an organic crystal, the interior being as densely packed as in a crystal lattice and the exterior being in contact with the solvent, water. Because of their charge properties, the polypeptide sequence motifs identified using the method of the present invention must occur mostly, if not exclusively, on the surface of a protein. Thus, all of the sequence motifs identified in human blood proteins using the selection process of the current invention are effectively always in contact with the immune system while the protein is in the blood. This holds for all conformations of the protein that might become populated in the bloodstream, including denatured states, because it is highly energetically unfavorable to transfer a charge from an aqueous medium to one-of low dielectric (as occurs in a protein interior). Accepted biochemical principles indicate, therefore, that the polypeptides designed from blood proteins using the method of the present invention will either not illicit an immune response or will elicit a minimal immune response. For the same reasons, polypeptides designed using the method of the present invention should be biocompatible. All sequence motifs identified from genomic data using the selection process of the current invention, not only those in blood proteins, should be biocompatible, though the extent of immune response or any other type of biological response may well depend on specific details of a sequence motif. (Because the polypeptide sequences on which the motifs are based actually occur in the organism for which the film as been fabricated, this approach will, at least in principle, work equally well for any type of organism. For instance, the approach may be of significant value to veterinary science.)

Both immune response and biocompatibility are important regarding the use of the designed peptides in biomedical applications, including, without limitation, the manufacture of artificial red blood cells, drug delivery systems, or polypeptides for fabrication of biocompatible films to coat implants for short-term or long-term introduction into an organism.

5. Bioactivity

In some applications of polypeptide thin films, coatings, or microcapsules, it may be desirable to modify the design of the polypeptides to include a functional domain for use in some layer of the structure, often the outermost. A functional domain in this context is an independently thermostable region of a protein that has specific biofunctionality (e.g. binding phosphotyrosine). It is well known in the art that such biofunctionality may be integrated with other functionalities in a multi-domain protein, as for example in the protein tensin, which encompasses a phosphotyrosine binding domain and a protein tyrosine phosphatase domain. The inclusion of such a domain in a designed polypeptide could function in a number of ways, including without limitation specific ligand binding, targeting in vivo, biosensing, or biocatalysis.

C. Uses for Polypeptides Designed Using the Method of the Present Invention

As noted above, polypeptides of suitable design are excellent materials for ELBL, and polypeptide film structures formed using ELBL will be useful in a large number of different types of applications. Polypeptides designed using the method of the present invention have been shown to be useful for ELBL of film structures for possible applications in biomedical technology, food technology, and environmental technology. For example, such polypeptides could be used to fabricate artificial red blood cells.

6. Artificial Red Blood Cells

A number of different approaches have been taken to red blood cell substitute development. One approach involves the use of perfluorocarbons. Perfluorocarbon emulsions contain synthetic fluorinated hydrocarbons capable of binding oxygen and delivering it to tissues. This approach however, increases reticulo-endothelial cell blockage. The perfluorocarbons can become trapped in the reticulo-endothelial system, which may result in adverse consequences.

Another approach focuses on antigen camouflaging, which involves coating red blood cells with a biocompatible polymer called polyethylene glycol (PEG). The PEG molecules form permanent covalent bonds on the surface of the cell. The coating effectively hides the antigenic molecules on the surface of the red blood cells, so that the blood recipient's antibodies do not recognize the cells as foreign. For example, the immune system of a normal person who has type A blood will naturally have antibodies that recognize antigens on the surface of type B red blood cells, leading to cell destruction. The attachment of PEG to the surface of a type B red blood cell "camouflages" the surface of the cell, so that its surface antigens can no longer be recognized by the immune system and the antigenically-foreign red blood cells will not be destroyed as quickly (see Pargaonkar, N. A., G. Sharma, and K. K. Vistakula. (2001) "Artificial Blood: Current Research Report," which is hereby incorporated by reference in its entirety).

A number of diseases, including thalassemia, that require repeated blood transfusions are often complicated by the development of antibodies to "minor" red cell antigens. This "allosensitization" can render these patients almost impossible to transfuse, rendering the situation life-threatening. In in vitro testing, the PEG-modified red cells appear not to trigger allosensitization and may also be useful in clinical situations where allosensitization has already occurred (see Scott, M. D. et al. (1997) "Chemical camouflage of antigenic determinants: Stealth erythrocytes," *Proc. Natl. Acad. Sci. USA.* 94 (14): 7566-7571, which is hereby incorporated by reference in its entirety).

Other approaches involve purified hemoglobin. Unmodified cell-free hemoglobin has known limitations. These include oxygen affinity that is too high for effective tissue oxygenation, a half-life within the intravascular space that is too short to be clinically useful, and a tendency to undergo dissociation into dimers with resultant renal tubular damage and toxicity. Because of these limitations, hemoglobin used to make a cell-free red blood cell substitute must be modified. A number of modification techniques have been developed. Hemoglobin can be cross-linked (a covalent bond between two molecules is made by chemical modification) and polymerized using reagents such as glutaraldehyde. Such modifications result in a product that has a higher $P_{50}$ (partial pressure of oxygen at which 50% of all oxygen-binding sites are occupied) than that of normal hemoglobin, and an increase in the plasma half-life of up to 30 hours. The source of the hemoglobin for this purpose can be human (outdated donated blood), bovine, or human recombinant. The solution of modified hemoglobin is prepared from highly purified hemoglobin and taken through various biochemical processes, to eliminate phospholipids, endotoxins, and viral contaminants (see Nester, T. and Simpson, M (2000) "Transfusion medicine update," *Blood Substitutes,* which is hereby incorporated by reference in its entirety). Biopure Corporation (Cambridge, Mass.) has been using modified hemoglobin for their product, Hemopure.

The main potential adverse effect of modified hemoglobin solutions is an increase in systemic and pulmonary vascular resistance that may lead to a decrease in cardiac index. Decreases in the cardiac index may impair optimum oxygen delivery and outweigh the advantage of an oxygen-carrying solution (see Kasper S. M. et al. (1998) "The effects of increased doses of bovine hemoglobin on hemodynamics and oxygen transport in patients undergoing preoperative hemodilution for elective abdominal aortic surgery," *Anesth. Analg.* 87: 284-91, which is hereby incorporated by reference in its entirety). One study has examined the utility of these solutions in the acute resuscitation phase of unstable trauma patients. Design of the study, however, was poor, and any role of the solutions in influencing ultimate patient outcome was unclear (see Koenigsberg D. et al. (1999) "The efficacy trial of diaspirin cross-linked hemoglobin in the treatment of severe traumatic hemorrhagic shock," *Acad. Emerg. Med.* 6: 379-80, which is hereby incorporated by reference in its entirety).

Many of the problems of cell-free hemoglobin can be overcome by encapsulating it with an artificial membrane. Liposomes are being used to encapsulate hemoglobin for use as a blood substitute. The approach is technically challenging because not only must the hemoglobin be prepared, it must be encapsulated in relatively high concentration and yield. The final products must be sterile and the liposomes must be relatively uniform in size.

Encapsulated hemoglobin has several advantages over cell-free hemoglobin. Firstly, the artificial cell membrane protects hemoglobin from degradative and oxidative forces in the plasma. Secondly, the membrane protects the vascular endothelium from toxic effects of hemoglobin. These relate to heme loss, the production $O_2$ free radicals and vasoconstrictor effects of NO binding. Thirdly, encapsulation greatly increases the circulating persistence of the hemoglobin. Moreover, encapsulated hemoglobin can be freeze-dried for convenient storage.

Liposomal encapsulation involves phospholipids, as in cell membranes. One major problem associated with liposomal encapsulation, however, is that it is very difficult to regulate the average size and distribution of liposomes. Another is that unlike red blood cells, liposomes are often not very stable, as they ordinarily lack an organized cytoskeleton. Yet another problem is that liposomes often consist of multiple layers of phospholipid. (A recent review of blood substitute development is presented in Stowell et al. (2001) Progress in the development of RBC substitutes, *Transfusion* 41:287-299, which is hereby incorporated by reference in its entirety. See also Chang, T. 1998 "Modified hemoglobin-based blood substitutes: cross linked, recombinant and encapsulated hemoglobin," *Artificial Cell* 74 Suppl 2:233-41, which is hereby incorporated by reference in its entirety.)

Red blood cell substitutes employing polypeptides designed using the method of the present invention should offer several advantages over approaches to the development of red blood cell substitutes known in the art, including, without limitation, superior oxygen and carbon dioxide binding functionality, lower production cost (large-scale and therefore low-cost production is possible because bacteria can be used to mass-produce the peptides and because peptide ELBL can be automated), the possibility of using suitable preparations of hemoglobin as a template for ELBL, polypeptide biodegradability, the immune "inertness" of designed polypeptides based on blood protein structure, and the structural stability exhibited by designed polypeptide films, which exceeds that of liposomes. Polypeptide ELBL assembly yields semi-porous films, minimizing the amount of material required for fabricating a means of encapsulation and enabling glucose, oxygen, carbon dioxide, and various metabolites to diffuse as freely through the films as a lipid bilayer. In contrast, other polymers potentially suitable for this purpose have undesirable side effects—for example, polylactide degrades into lactic acid, the substance that causes muscle cramps, and poly (styrene sulfonate) is not biocompatible.

Microcapsules could be formed of designed polypeptides to encapsulate hemoglobin to serve as a red blood cell substitute. Hemoglobin polypeptide microcapsules could also be engineered to incorporate enzymes, including superoxide dismutase, catalase, and methemoglobin reductase, which are ordinarily important for red blood cell function. Moreover, the nanofabricated microcapsules can predictably be dehydrated, suggesting that artificial red blood cells made as described herein could be dehydrated, without loss of function, particularly because hemoglobin can be lyophilized (i.e., freeze-dried) and reconstituted without loss of function, and polyion films are stable to dehydration. This will be important for long-term storage, transport of blood substitutes, battlefield applications (particularly in remote locations), and space exploration.

Polypeptides designed using the method of the present invention could also be used for drug delivery.

7. Drug Delivery

Micron-sized "cores" of a suitable therapeutic material in "crystalline" form can be encapsulated by designed polypeptides, and the resulting microcapsules could be used for drug delivery. The core must be insoluble under some conditions, for instance high pH or low temperature, and soluble under the conditions where controlled release will occur. The surface charge on the crystals can be determined by $\zeta$-potential measurements (used to determine the charge in electrostatic units on colloidal particles in a liquid medium). The rate at which microcapsule contents are released from the interior of the microcapsule to the surrounding environment will depend on a number of factors, including the thickness of the encapsulating shell, the polypeptides used in the shell, the presence of disulfide bonds, the extent of cross-linking of peptides, temperature, ionic strength, and the method used to assemble the peptides. Generally, the thicker the capsule, the longer the release time—the principle resembles that of gel filtration chromatography.

Some work has been done on sustained release from ELBL microcapsules (see Antipov, A., Sukhorukov, G. B., Donath, E., and Möhwald, H. (2001) *J. Phys. Chem. B*, 105:2281-2284 and Freemantle, M. (2002) Polyelectrolyte multilayers, *Chem. Eng. News*, 80: 44-48, both of which are incorporated herein by reference in their entireties). Polyelectrolytes that have been used are PSS, PAH, PAA, PVS, PEI, and PDDA.

Polypeptides designed using the method of the present invention should offer a number of advantages in the context of drug delivery, including without limitation control over the physical, chemical, and biological characteristics of the microcapsule; the ability to make capsules with a diameter of less than 1 mm, making the capsules suitable for injection; low likelihood of eliciting an immune response; generally high biocompatibility of capsules; control over the diffusive properties of the microcapsules by varying the thickness of the layers and using cysteine, as discussed below; the ability to target specific locations by modification of the microcapsule surface using the highly reactive sulhydryl groups in cysteine (as is well known in the art, free sulfhydryl groups, free amino groups, and free carboxyl groups are sites to which molecules for specific targeting could be attached), or by incorporation of a specific functional domain in the design of the polypeptide; and the ability of microstructures to be taken up by cells using either endocytosis or pinocytosis.

Polypeptides designed using the method of the present invention could also be used for antimicrobial coatings.

8. Antimicrobial Coatings

The method of the present invention could be used to manufacture films encompassing antimicrobial peptides. For example, one suitable sequence might be Histatin 5, which occurs in humans:

```
                                        (SEQ ID NO:8)
Asp Ser His Ala Lys Arg His His Gly Tyr Lys Arg

Lys His Glu Lys His His Ser His Arg Gly Tyr
```

The preponderance of positive charge at slightly basic pH makes this sequence quite suitable for ELBL. It could be appended to a peptide designed using the method of the present invention, resulting in an antimicrobial peptide suitable for use in ELBL. This peptide could be used as an anti-biofouling coating. For instance, the peptide could be used to form a coating on devices used for implantation.

There are also a number of other areas in which polypeptides designed using the method of the present invention could be useful.

9. Other Uses

Other possible uses for peptides designed using the method of the present invention include without limitation food covers, wraps, and separation layers; food casings, pouches, bags, and labels; food coatings; food ingredient microcapsules; drug coatings, capsules, and microcapsules; disposable food service items (plates, cups, cutlery); trash bags; water-soluble bags for fertilizer and pesticides; microcapsules for fertilizer and pesticides; agricultural mulches; paper coatings; loose-fill packaging; disposable medical products (e.g. gloves and gowns); and disposable diapers.

B. Fabrication

Once amino acid sequence motifs have been selected from those identified using the method discussed in Part VII(B)(1) above or designed de novo, the designed polypeptide is synthesized using methods well known in the art, such as solid phase synthesis and F-moc chemistry or heterologous expression following gene cloning and transformation. Designed polypeptides may be synthesized by a peptide synthesis company, for example SynPep Corp. (Dublin, Calif.), produced in the laboratory using a peptide synthesizer, or produced by recombinant methods.

In one embodiment, a designed polypeptide, e.g., a first layer polypeptide, comprises a plurality of individual amino acid sequence motifs joined in tandem. The same motif may be repeated, or different motifs may be joined in designing a polypeptide for ELBL. Amino acids such as glycine or proline could be used to link the sequence motifs, so long as the overall charge properties of the polypeptide are maintained, that is, the net charge on the polypeptide per residue is 0.5. In one embodiment, a linker comprises 1-4 amino acid residues, for example, 1-4 glycine or proline resides. In addition, amino acids other than the 20 usual ones could be included in the motifs themselves, depending on the properties desired of the polypeptide. Other properties could likewise be specified by design requirements, using methods known in the art. For example, proline could be included for turn formation, glycine for chain flexibility, and histidine for pH-sensitive charge properties near neutral pH. "Hydrophobic" amino acids could also be included—hydrophobic residue content could play a role in assembly behavior and contribute to layer stability in a way resembling the hydrophobic stabilization of globular proteins.

Figure 12:
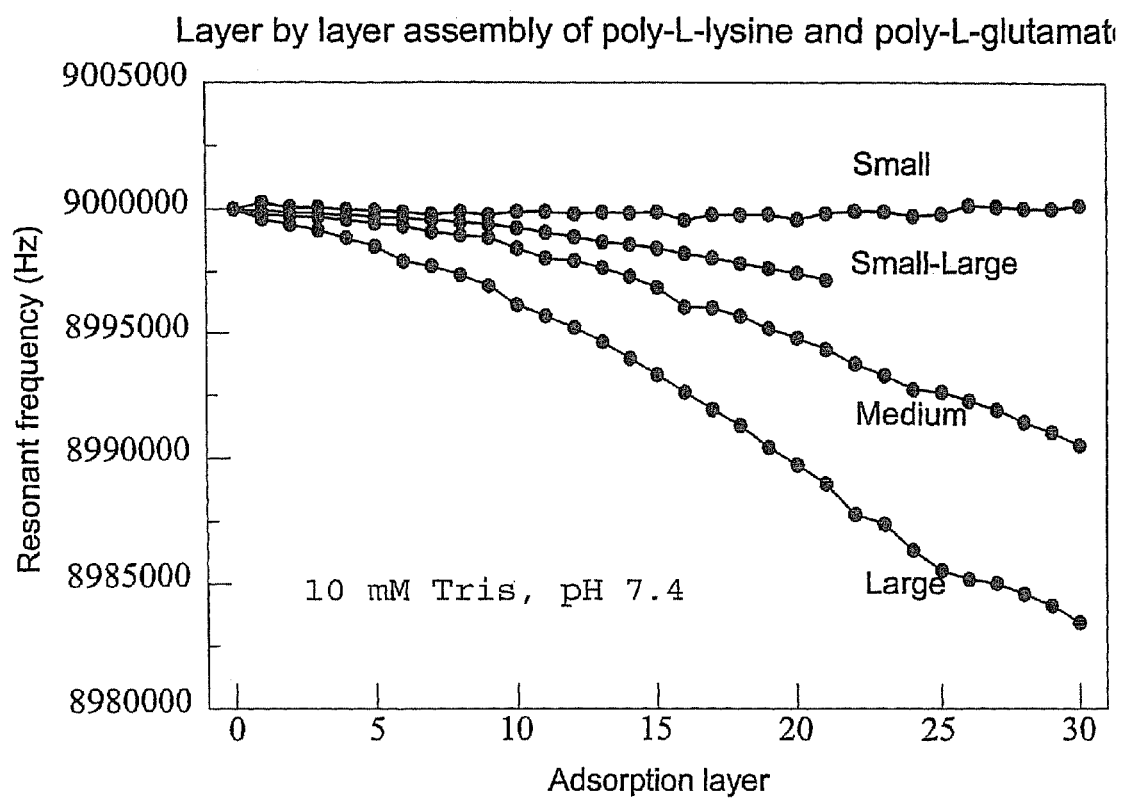
FIG. 12 shows adsorption data for polyelectrolytes of different lengths, illustrating that long polyelectrolytes adsorb better than short ones.

In one embodiment, a designed polypeptide is greater than or equal to 15 amino acid residues long. In other embodiments, a designed polypeptide is greater than 18, 20, 25, 30, 32 or 35 amino acids long. The reason for this is that the entropy loss per molecule is so thermodynamically unfavorable for short polymers that adsorption to an oppositely-charged surface is inhibited, even if the polypeptide has a charge per unit length of 1; long polyelectrolytes adsorb better than short ones. This is illustrated in FIG. 12. The average molecule masses of the peptides utilized for the length-dependence studies were 1,500-3,000 Da (poly-L-glutamate, "small"), 3,800 Da (poly-L-lysine, "small"), 17,000 Da (poly-L-glutamate, "medium"), 48,100 Da (poly-L-lysine, "medium"), 50,300 Da (poly-L-glutamate, "large"), and 222,400 Da (poly-L-lysine, "large"). The data shown in FIG. 12 clearly indicate that ELBL depends on length of peptide. Inclusion of Cys enables the use of relatively small peptides for ELBL, because the sulfhydryl group can be used to form disulfide crosslinks between polypeptides.

C. Film Assembly

A method of making a designed polypeptide multilayer film comprises depositing a plurality of layers of oppositely charged chemical species on a template, wherein at least one layer comprises a designed polypeptide. Successively deposited polyelectrolytes will have opposite net charges. In one embodiment, deposition of a designed polypeptide (or other polyelectrolyte) comprises exposing the substrate to an aqueous solution comprising a designed polypeptide (or other polyelectrolyte) at a pH at which it has a suitable net charge for ELBL. In other embodiments, the deposition of designed polypeptide or other polyelectrolyte on the substrate is achieved by sequential spraying of solutions of oppositely charged polypeptides. In yet other embodiments, deposition on the substrate is by simultaneous spraying of solutions of oppositely charged polyelectrolytes.

In the ELBL method of forming a multilayer film, the opposing charges of the adjacent layers and the gain in entropy on release of counterions to solution together provide the driving force for assembly. It is not critical that polyelectrolytes in opposing layers have the same net linear charge density, only that opposing layers have opposite charges. The standard film assembly procedure includes forming aqueous solutions of the polyions at a pH at which they are ionized (i.e., pH 4-10), providing a substrate bearing a surface charge, and alternating immersion of the substrate into the charged polyelectrolyte solutions. The substrate is optionally washed in between deposition of alternating layer.

The concentration of polyion suitable for deposition of the polyion can readily be determined by one of ordinary skill in the art. An exemplary concentration is 0.1 to 10 mg/ml. Typically, the thickness of the layer produced is substantially independent of the solution concentration of the polyion during deposition in the stated range. For typical non-polypeptide polyelectrolytes such as poly(acrylic acid) and poly(allylamine hydrochloride), typical layer thicknesses are about 3 to about 5 Å, depending on the ionic strength of solution. Short polyelectrolytes typically form thinner layers than long polyelectrolytes. Regarding film thickness, polyelectrolyte film thickness depends on humidity as well as the number of layers and composition of the film. For example, PLL/PLGA films 50 nm thick shrink to 1.6 nm upon drying with nitrogen. In general, films of 1-2 nm to 100 nm or more in thickness can be formed depending on the hydration state of the film and the molecular weight of the polyelectrolytes employed in the assembly.

Experiments

1. EXAMPLE 1

Design of Polypeptides Based on Human Blood Protein Sequences and their Use in Polypeptide Film Fabrication For this work, amino acid sequences were selected using the process described in Part VII(B)(1) above to identify sequence motifs in the primary structure of human blood proteins: Complement C3 (gi|68766) was the source of the anionic sequence motifs, and lactotransferrin (gi|4505043) the source of the cationic sequence motifs. As discussed above, blood protein sequences were used to minimize the immune response of patients into whom devices involving the polypeptides might be introduced (including, e.g. artificial red blood cells). In principle, this approach should be applicable for any organism having an immune system; it is not limited to humans. Polypeptides were synthesized by SynPep Corp. (Dublin, Calif.). The polypeptide sequences were:

```
                                              (SEQ ID NO:2)
Tyr Glu Glu Asp Glu Cys Gln Asp Gly Glu Glu Asp

Glu Cys Gln Asp Gly Glu Glu Asp Glu Cys Gln Asp

Gly Glu Glu Asp Glu Cys Gln Asp (SEQ ID NO:1)
Tyr Arg Arg Arg Arg Ser Val Gln Gly Arg Arg Arg

Arg Ser Val Gln Gly Arg Arg Arg Arg Ser Val Gln

Gly Arg Arg Arg Arg Ser Val Gln
```

```
                  -continued
                                              (SEQ ID NO:4)
Tyr Glu Glu Asp Glu Cys Gln Asp Gly Glu Glu Asp Glu Cys Gln Asp Gly Glu Glu Asp Glu Cys Gln Asp Gly Glu Glu Asp Glu Cys Gln Asp Gly Glu Glu Asp Glu Cys Gln Asp Gly Glu Glu Asp Glu Cys Gln Asp (SEQ ID NO:3)
Tyr Arg Arg Arg Arg Ser Val Gln Gly Arg Arg Arg Arg Ser Val Gln Gly Arg Arg Arg Arg Ser Val Gln Gly Arg Arg Arg Arg Ser Val Gln Gly Arg Arg Arg Arg Ser Val Gln Gly Arg Arg Arg Arg Ser Val Gln
```

The amino acid residues are represented by the three-letter code given above. One glycine was introduced between each 7-residue motif to inhibit secondary structure formation. Glycine was selected for this purpose because it allows the greatest variability in combination of dihedral angles (see Ramachandran, G. N. and Saisekharan, V. (1968), *Adv. Prot.ein Chem.istry*, 23:283, which is incorporated by reference herein in its entirety) and has a low helix propensity (0.677) and low sheet propensity (0.766). Alternatively, proline could be substituted for glycine between motifs on the basis of calculated structure propensities. Additionally, a single tyrosine was included at the N-terminus of each peptide for concentration determination by UV absorption at 280 rm. SEQ ID NO:2 has a balance of charge of 20/32 (0.625) at pH 7; SEQ ID NO:1 has a balance of charge of 16/32 (0.5); SEQ ID NO:4 has a balance of charge of 30/48 (0.625) at pH 7; and SEQ ID NO:3 has a balance of charge of 24/48 (0.5) at pH 7. In all cases, the balance of charge is greater than or equal to approximately one-half of the total length of the first layer polypeptide at pH 7.

The polypeptides were named SN1 (SEQ ID NO: 2), SP2 (SEQ ID NO: 1), LN3 (SEQ ID NO: 4), and LP4 (SEQ ID NO: 3), respectively, meaning short negative, short positive, long negative, and long positive. These sequences are quite different from polylysine (commonly used in the art as a polycation) and polyglutamate (commonly used in the art as a polyanion) which, though available commercially and inexpensive, have a high α-helix propensity under conditions of mild pH and, crucially, are immunoreactive. The calculated charge per unit length on the designed peptides at neutral pH is 0.5 electrostatic units for SP and LP and 0.6 electrostatic units for SN and LN. The positive peptides are somewhat more hydrophobic than the negative ones, owing to the presence of valine and the long hydrocarbon side chain of arginine. (As mentioned above, hydrophobic interactions between polypeptide layers could stabilize films to some extent.) The lengths are consistent with published studies showing that polyions must have greater than 20 charged groups (i.e. aspartic acid and glutamic acid; lysine, arginine, and histidine) to be suitable for ELBL (see Kabanov, V. and Zezin, A. (1984) *Pure Appl. Chem.* 56:343 and Kabanov, V. (1994) *Polym. Sci.* 36:143, both of which are incorporated by reference herein in their entireties).

a. Experimental demonstration i. Materials

QCM electrodes (USI-System, Japan) coated with evaporated silver had a surface area of $0.16\pm0.01$ cm$^2$ on each side, a resonant frequency of 9 MHz (AT-cut), and a long-term stability of $\pm 2$ Hz. The polypeptide molecular weight was verified by electrospray mass spectrometry. Peptide purity was greater than 70%. The polypeptide buffer was 10 mM sodium phosphate or 10 mM Tris-HCl, 1 mM DTT, 0.1 mM sodium azide, pH 7.4. All chemicals other than polypeptides were purchased from Sigma-Aldrich (USA).

ii. Procedures

Figure 3A:
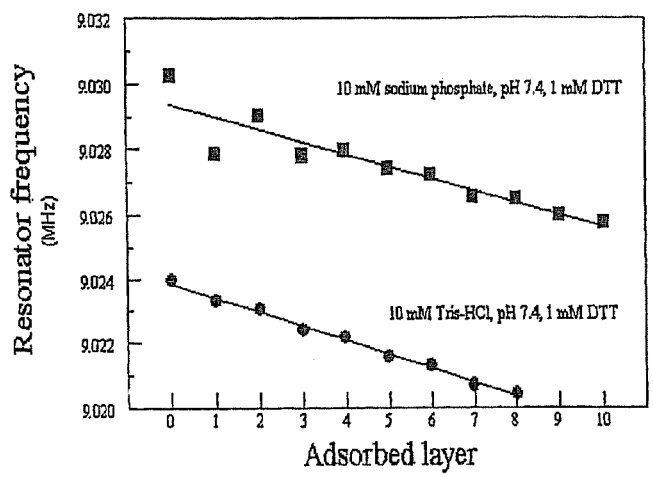
FIG. 3(a) shows adsorption data as monitored by the quartz crystal microbalance technique ("QCM") for a combination of amino acid sequences designed according to the present invention.
Figure 3B:
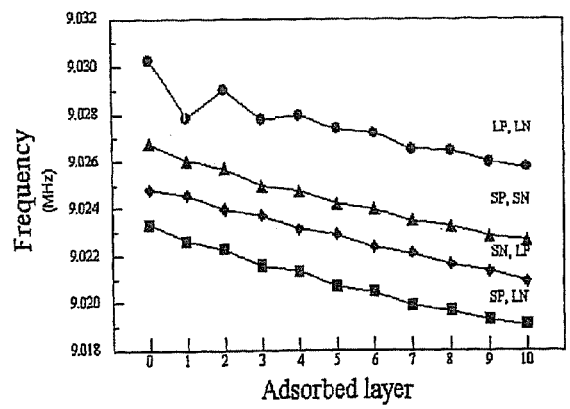
FIG. 3(b) shows a comparison of adsorption data as monitored by QCM for different combinations of amino acid sequences designed according to the present invention.
Figure 3C:
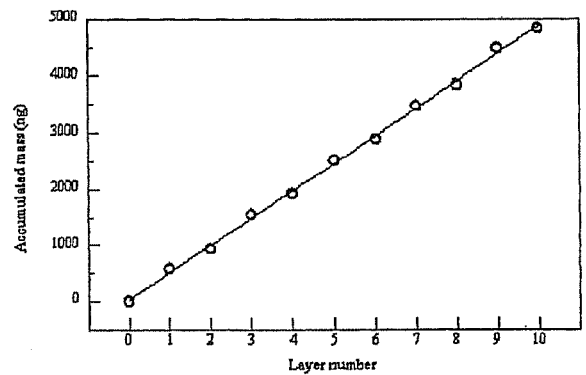
FIG. 3(c) shows a graph of adsorbed mass in nanograms versus layer number for amino acid sequences designed and fabricated according to the present invention.

Experiments were done using pairs of designed polypeptides, one negative and one positive. Multilayer films consisting of at least 5 bi-layers of the above-identified SP2, SN1, LP4, and LN3 were deposited onto the QCM resonators using standard ELBL techniques (a bi-layer consists of one layer of polycation and one layer of polyanion). The polypeptide concentration used for layer adsorption was 2 mg·mL$^{-1}$. It is known that dependence of polyion layer thickness on polyelectrolyte concentration is not strong (see Lvov, Y. and Decher, G. (1994) *Crystallog. Rep.* 39:628, which is incorporated herein by reference in its entirety); in the concentration range 0.1 to 5 mg mL$^{-1}$, bilayer thickness was approximately independent of concentration for PSS/PAH. By contrast, polypeptide thin films appear substantially less thick than those fabricated using high molecular weight PSS/PAH (mass calculated using $\Delta f$ data using the well-known Sauerbrey equation); see Lvov, Y. and Decher, G. (1994) *Crystallog. Rep.* 39:628. This follows from calculating film thickness on the basis of mass deposited, as is ordinarily done in the art for proteins. The calculated thickness for the designed polypeptide assembly shown in FIG. 3(c) is greater than the end-to-end length of the peptides used to make the film. DTT was included at 1 mM to inhibit disulfide bond formation. The adsorption time was 20 minutes.

Resonators were rinsed for 1 min. in pure water between subsequent adsorption cycles (removing perhaps 10-15% of weakly adsorbed material) and dried in a stream of gaseous $N_2$. Then the mass of the deposited peptide was measured indirectly by QCM. The mass measurement includes some water, despite drying, and low mass ions like $K^+$, $Na^+$, and $Cl^-$. Partial interpenetration of neighboring layers of peptide is probable (see Decher, G. (1997) *Science* 227:1232; Schmitt et al. (1993) *Macromolecules* 26:7058; and Komeev et al. (1995) *Physica B* 214:954); this could be important for the efficiency of disulfide "locking."

iii. Results

After adsorption of the polypeptide and rinsing and drying the QCM resonator, the resonant frequency of the resonator was measured. This enabled calculation of the frequency shift on adsorption and change in adsorbed mass. A decrease in frequency indicates an increase in adsorbed mass. The results are provided in FIGS. 3(a) and 3(b). FIG. 3(a) shows a comparison of adsorption data for LP4 and LN3 in different buffers (10 mM sodium phosphate, pH 7.4, 1 mM DTT and 10 mM Tris-HCl, pH 7.4, 1 mM DTT). It is clear from these data that adsorption depends more on the properties of the peptides than the specific properties of the buffer used. FIG. 3(b) shows resonator frequency versus adsorbed layer for different combinations of SP2, SN1, LP4, and LN3 (namely, SP2/SN1, SP2/LN3, LP4/SN1, and LP4/LN3) in 10 mM sodium phosphate, pH 7.4 and 1 mM DTT (the lines merely connect experimental data points). Each of these combinations involved one negative polypeptide and one positive polypeptide, as required by ELBL. FIG. 3(c) shows a graph of calculated adsorbed mass versus layer number for SN1 and LP4 in 10 mM Tris-HCl, pH 7.4 and 1 mM DTT (calculated from experimental data using the Sauerbrey equation). The total adsorbed mass, approximately 5 µg, corresponds approximately to 1 nmol of peptide. The equation used for this calculation was $\Delta m = -0.87 \cdot 10^{-9} \, \Delta f$ where m is mass in grams and f is frequency in Hz (see Lvov, Y., Ariga, K., Ichinose, I., and Kunitake, T. (1995) *J. Am. Chem. Soc.* 117:6117 and Sauerbrey, G. (1959) *Z. Physik* 155:206, both of which are incorporated herein by reference in their entireties). Film thickness, d, is estimated as $d = -0.016 \Delta f$ where d is in nm (see Yuri Lvov, "Electrostatic Layer-by-Layer Assembly of Proteins and Polyions" in *Protein Architecture: Interfacial Molecular Assembly and Immobilization Biotechnology*, (Y. Lvov & H. Möhwald eds., 2000) (New York: Dekker, 2000) pp. 125-167, which is incorporated herein by reference). The line in FIG. 3(c) is a linear fit to experimental data points. The linearity of the data is a likely indicator of precise, regular assembly during adsorption and an approximately uniform density of the polypeptides in each adsorbed layer. Adsorption occurred with a frequency shift of $-610 \pm 60$ Hz (cations) or $-380 \pm 40$ Hz (anions). Linear growth of deposited polypeptide mass indicates repeatability of adsorption steps early in the assembly process and the general success of the multilayer fabrication process.

iv. Conclusions

The above results show that polypeptides designed using the method of the present invention are suitable for ELBL, despite significant qualitative differences from PSS and PAH, flexible homopolymers having 1 charge per unit length at pH 7.4. The charge per unit length on poly-L-lysine and poly-L-glutamic acid is 1 at pH 7.4, as with PSS and PAH, but both of these polypeptides have a marked propensity to form α-helical structure under various conditions, making them substantially less suitable for multilayer assembly when control over thin film structure is desired. The monodisperse polypeptides of the present invention, however, enable the practitioner to know, quite precisely, the structure of the material being used for ELBL. Moreover, usual commercial preparations of poly-L-lysine and poly-L-glutamic acid are polydisperse, and poly-L-lysine, poly-L-glutamic acid, PSS, and PAH evoke an immune response (i.e. are immunogenic) in humans.

Because the designed polypeptides are readily adsorbed on an oppositely charged surface, as demonstrated by experiment, there is no need for a "precursor" layer. As is known in the art, "precursor" layers are deposited on a substrate to enhance adsorption of less adsorptive substances. The lack of a precursor layer enhances the biocompatibility of the polyion films because polymers ordinarily used as precursors are immunogenic or allow less precise control over polymer structure or thin film structure than designed polypeptides.

Multilayers of the designed polypeptides were stable at the pH of human blood, 7.4. Thus, the multilayers should be useful for a broad range of biological applications. Adsorption of the designed polypeptides, each of less than 1 charge per residue, was essentially complete in less than 10 min. at 2 mg/mL and low ionic strength. This implies that these polypeptides can be used to form multilayer films quickly and with relative ease. Drying the peptide film with $N_{2(g)}$ after deposition of each layer did not impair assembly. Drying is done to get an accurate QCM frequency measurement, but is not required for assembly.

Figure 7:
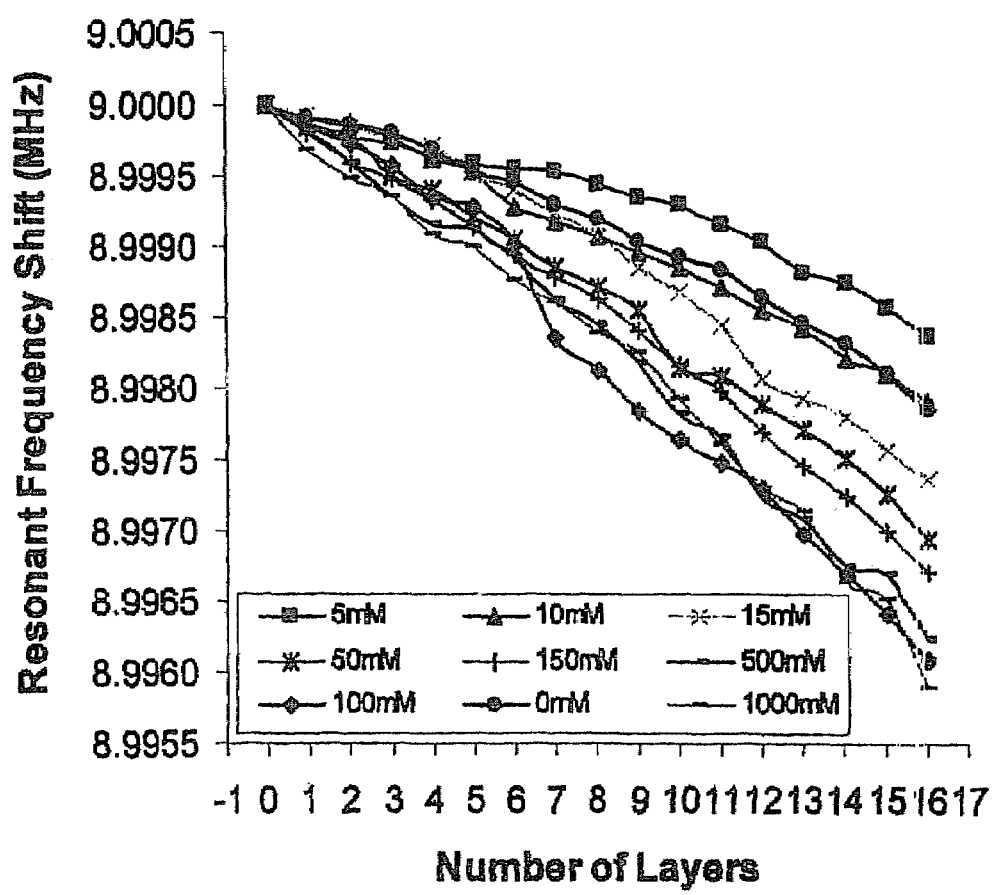
FIG. 7 shows the ELBL adsorption of poly-L-glutamate and poly-L-lysine from an aqueous medium as a function of ionic strength.

The film assembly experiments were done at a lower ionic strength than that of blood, but the process gives a qualitatively similar result at higher ionic strength. The chief difference is the amount of peptide deposited per adsorption layer—the higher the ionic strength, the greater the amount of peptide deposited. This is illustrated by the graph in FIG. 7, which shows the amount of material deposited as a function of ionic strength—the peptides used were poly-L-glutamic acid and poly-L-lysine. QCM resonant frequency is plotted against adsorption layer. The average molecular mass of poly-L-glutamate was 84,600 Da, while that of poly-lys was 84,000 Da. The peptide concentration used for assembly was 2 mg/mL. The data indicate salt concentration (ionic strength of solution) influences thin film assembly. In general, the amount of material deposited per layer increases with ionic strength in the range 0-100 mM NaCl. As the essential character of ELBL with designed polypeptides appears not to depend on the choice of buffer under conditions of relatively high net charge per unit length and low ionic strength, qualitatively similar results are expected at the ionic strength of human blood. Thus, the choice of buffer should not fundamentally alter the stability of the multilayers in their target environment. However, even if the choice of buffer did affect the stability of the multilayers, the "locking" mechanism would be available as a design feature to stabilize the capsule.

The greater apparent deposition of positive polypeptides than negative ones may result from the higher charge per unit length on the positive polypeptides at pH 7.4. The material deposited in each layer probably corresponds to that required for neutralization of the charge of the underlying surface. Hydrophobic interactions could also help to explain this feature of adsorption behavior.

The usual thin film thickness calculation for proteins and other polymers is probably invalid for short polypeptides (calculated thickness is 60-90 nm, but summed length of 10 polypeptides is approximately 120 nm). This probably results from a high density of packing of the relatively short polypeptides onto the adsorption surface; the result is also consistent with finding that film thickness varies with ionic strength, as changes in structural properties of a polymer will occur and screening of charges by ions will reduce intra-layer charge repulsion between adsorbed peptides. The thickness of the designed polypeptide thin film discussed here is estimated at 20-50 nm.

Many aspects of the design and fabrication cycles could be automated. For example, a computer algorithm could be used to optimize the primary structure of peptides for ELBL by comparing predicted peptide properties with observed physical properties, including structure in solution, adsorption behavior, and film stability at extremes of pH. Moreover, the polypeptide film assembly process can be mechanized, once the details of the various steps have been sufficiently determined.

2. EXAMPLE 2

Experiments Involving De Novo-Designed Polypeptides Containing Cysteine a. Polypeptides
The polypeptides used were:

```
                                                    (SEQ ID NO:5)
Tyr Lys Cys Lys Gly Lys Val Lys Val Lys Cys Lys

Gly Lys Val Lys Val Lys Cys Lys Gly Lys Val Lys

Val Lys Cys Lys Gly Lys Val Lys (SEQ ID NO:6)
Tyr Glu Cys Glu Gly Glu Val Glu Val Glu Cys Glu

Gly Glu Val Glu Val Glu Cys Glu Gly Glu Val Glu

Val Glu Cys Glu Gly Glu Val Glu
```

Unlike the other polypeptides used in the experiments described herein, these two were not designed using human genome information; they were designed de novo for the sole purpose of assessing the role of disulfide bond formation in polypeptide film stabilization. SEQ ID NO:5 has a balance of charge of 16/32 (0.5) at pH 7; and SEQ ID NO:6 has a balance of charge of 16/32 (0.5) at pH 7. In both cases, the balance of charge is greater than or equal to approximately one-half of the total length of the first layer polypeptide at pH 7.

Procedures

All experiments were conducted at ambient temperature.

All assembly experiments using QCM were conducted in the same conditions, except that the samples to undergo oxidation were dried using air instead of nitrogen gas. The assembly conditions were 10 mM Tris-HCl, 10 mM DTT, pH 7.4. The nominal peptide concentration was 2 mg/ml. The number of layers formed was 14.

Disulfide locking conditions for the oxidizing samples were 10 mM Tris-HCl, 1% DMSO, saturation of water with air, pH 7.5. The duration of the "locking" step was 6 hours. Conditions for the reducing samples were 10 mM Tris-HCl, 1 mM DTT, saturation of water with nitrogen, pH 7.5. The duration of this step was 6 hours.

All disassembly experiments using QCM were conducted in the same conditions, except that the oxidizing samples were dried using air instead of nitrogen. Disassembly conditions were 10 mM KCl, pH 2.0 Samples were rinsed with D.I. water for 30 seconds prior to drying.

Three different types of experiments were conducted: (1) Reducing—no treatment: disassembly was conducted immediately after assembly; (2) Reducing—6 hours, as described above for reducing samples; and (3) Oxidizing—6 hours, as described above for oxidizing samples.

b. Results

Figure 10:
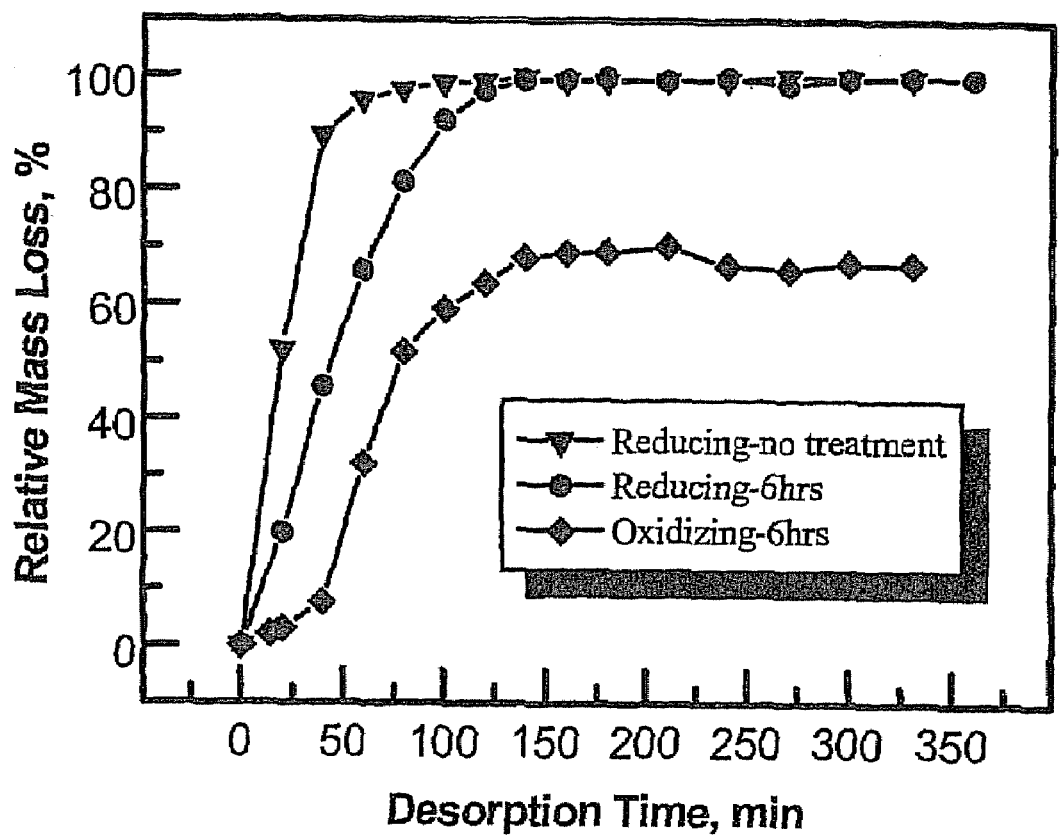
FIG. 10 shows the percentage of material lost during the acidic pH disassembly step of an experiment involving de novo-designed polypeptides containing cysteine.

The results are illustrated in FIG. 10. In the first two experiments (both reducing), all of the deposited material (100%) disassembled within 50 minutes. By contrast, in the oxidizing experiment, a substantial amount of material remained after substantial incubation of the peptide film-coated QCM resonator at pH 2 for over 5 hours. The stability of the polypeptide films at acidic pH is determined by the conditions of assembly; in this way, film or capsule stability is a design feature that becomes possible by using polypeptides as the polyelectrolytes for ELBL.

c. Conclusions

Electrostatic forces play a key role in holding together oppositely-charged layers of designed polypeptides. At acidic pH, the net charge on one of the peptides is neutralized and the polypeptide film disassembles due to electrostatic repulsion. Reducing conditions prevent disulfide bond formation. Therefore, the electrostatic attraction between the layers is the only binding force for stabilizing the layers under these conditions. By contrast, under oxidizing conditions disulfide bonds are formed. At acidic pH, disulfide bonds inhibit film disassembly. The results indicate that layer stability at acidic pH is directly affected by the formation of intra- and/or inter-layer disulfide bonds—i.e. between molecules in the same layer, between molecules in adjacent layers, or both. This is illustrated by the results shown in FIG. 10—due to disulfide locking, more than 30% of the film remained stable at acidic pH, despite electrostatic repulsion at relatively low ionic strength. Peptides with more cysteine residues are anticipated to further improve disulfide locking efficiency. Moreover, adjustment of the conditions of peptide assembly will be an important aspect of engineering films to have the desired physical as well as chemical and biological properties.

3. EXAMPLE 3

Experiments Involving Designed Polypeptides Containing Cysteine a. Materials

The essential elements of this experiment were a quartz crystal microbalance instrument; silver-coated resonators (9 MHz resonant frequency); the negative 48-residue peptide (LN3) (SEQ ID NO: 4); and a positive 48-residue peptide named "SP5" of the following sequence:

```
                                              (SEQ ID NO:7)
Tyr Lys Gly Lys Lys Ser Cys His Gly Lys Gly Lys

Lys Ser Cys His Gly Lys Gly Lys Lys Ser Cys His

Gly Lys Gly Lys Lys Ser Cys His
```

Like the other designed peptides discussed above in Part VII(E)(1), SP5 was designed using the process described above in Part VII(B)(1) to analyze the amino acid sequence of the human blood protein lactotransferrin (gi|4505043). The ELBL buffer was 10 mM Tris, pH 7.4, 10 mM NaCl, and 1 mM DTT. The disassembly buffer was 10 mM KCl, pH 2. 2 mL peptide solutions were prepared for SP5 and LN3 by adding 4 mg of each peptide to 2 mL of the above buffer solution and adjusting the pH of each solution to 7.4; the peptide concentration was 2 mg-mL$^{-1}$.

b. Procedure for Monitoring Assembly of Polypeptide Layers on QCM Resonators

Reducing procedures were as follows: (1) The frequency of the resonator was measured and recorded prior to peptide adsorption; (2) The resonator was dipped into the SP5 peptide solution for 20 min.; (3) The resonator was dipped into the SP5 rinse solution for 30 sec.; (4) The resonator was removed from the rinse solution and dried using nitrogen gas; (5) The QCM resonant frequency of the resonator was recorded; (6) The resonator was dipped into the LN3 peptide solution for 20 min.; (7) The resonator was dipped into the LN3 rinse solution for 30 sec.; (8) The resonator 1 was removed from the rinse solution and dried using nitrogen gas; (9) The QCM resonant frequency of the resonator was recorded; (10) Steps 2 through 9 were repeated until 16 layers were adsorbed onto the resonator.

Oxidizing procedures were the same as the reducing procedures, except that the resonator was rinsed in D.I. water instead of the SP5 buffer or the LN3 buffer and dried with air instead of nitrogen before each measurement.

c. Locking Procedures

Reducing procedures were as follows: The resonator was placed in an aqueous solution containing 1 mM DTT for 6 hours. DTT, a reducing agent, inhibited disulfide bond formation.

Oxidizing procedures were as follows: The resonator was placed in an air-saturated aqueous solution containing 1% DMSO for 6 hours. DMSO, an oxidizing agent, promoted disulfide bond formation.

d. Disassembly on Resonator i. Solutions

Reducing conditions were as follows: 10 mM KCl, 1 mM DTT, pH 2.

Oxidizing conditions were as follows: 10 mM KCl, 20% DMSO, pH 2.

ii. Procedure for Disassembly

Reducing procedures were as follows: (1) The initial resonant frequency of the resonator was measured by QCM and recorded; (2) The resonator was dipped into the reducing disassembly solution for 5 min.; (3) The resonator was rinsed in reducing buffer solution for 30 sec.; (4) The resonator was dried with gaseous N$_2$; (5) The resonant frequency of the resonator was measured by QCM and recorded; (6) Steps 2 through 5 were repeated for reading times of 5, 10, 15, 20, 30, 60, and 90 min.

Oxidizing procedures were the same as for reducing procedures, except that rinsing of the resonator was done in D.I. water saturated with air instead of reducing buffer.

e. Results

Figure 8:
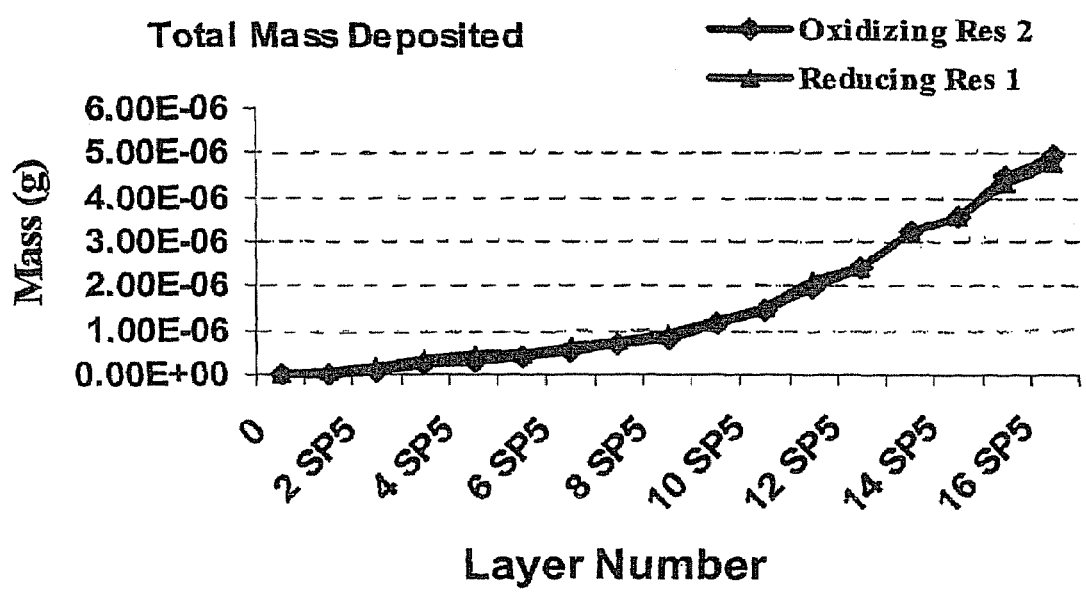
FIG. 8 shows the adsorption of polypeptides designed according to the method of the present invention for experiments to probe the effect of disulfide bond formation.

FIG. 8 shows approximately linear increase in mass deposited during thin film assembly of SP5 and LN3. Both resonators show almost identical deposition of mass throughout the process of assembly, despite differences in assembly conditions.

Figure 9:
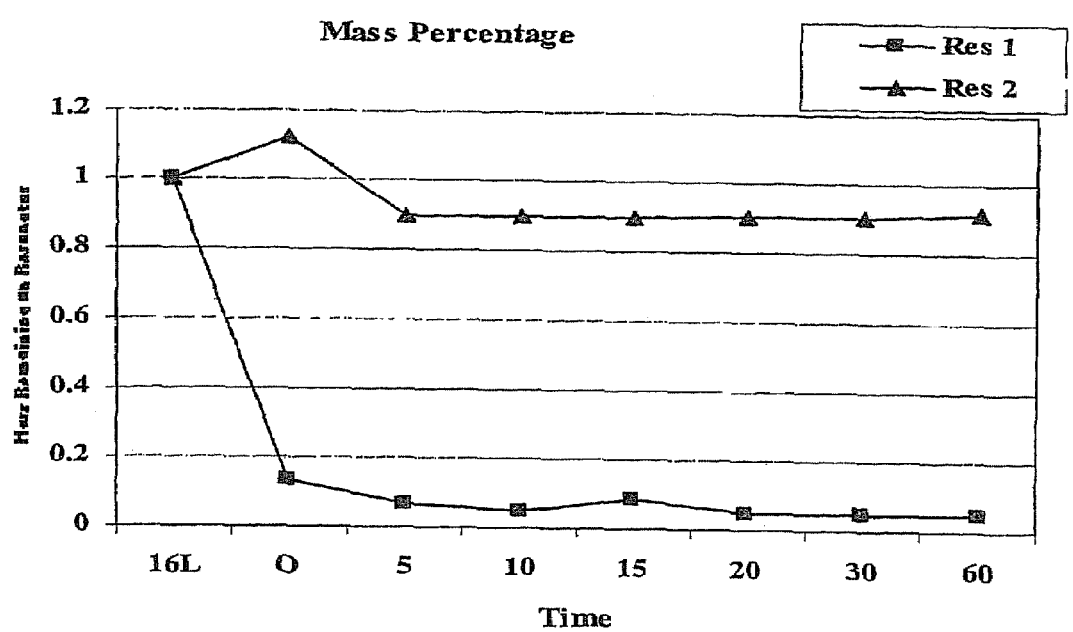
FIG. 9 shows the percentage of material remaining during thin film disassembly at acidic pH as discussed with reference to FIG. 8.

FIG. 9 shows the percentage of material remaining during film disassembly. The layers subjected to oxidizing conditions showed a minimal loss of material at acidic pH with almost 90 to 95% of mass retention. By contrast, layers subjected to reducing conditions lost almost all the film material within the first 5 minutes of exposure to acidic pH.

f. Conclusions

The results demonstrate that at acidic pH, disulfide bonds prevent layer degeneration and hold the layers firmly together. Layer stability at acidic pH is directly affected by the formation of intra- and/or inter-layer disulfide bonds. Disulfide bond formation is dependent on the concentration and proximity of cysteine residues to each other. Increasing the concentration per unit chain length of the polypeptide would therefore directly influence disulfide bond formation and thin film stability. Increasing the ionic strength of the buffer solutions used for film assembly influences the concentration of cysteine in the film by increasing the amount of material deposited per adsorption cycle and the thickness of each layer. The increased number of cysteine amino acids in a single layer would in this way increase the number of disulfide bonds formed, and, on oxidation, increase film stability.

4. EXAMPLE 4

Films with Heterogeneous Layers

A designed polycationic peptide multilayer film containing a non-peptidic polyanion, in this case poly(acrylic acid) (PAA). The polypeptide film is made of a suitable designed peptidic polycation, e.g., KVKGKCKVKVKGKCK-VKVKGKCKVKVKGKCKY (SEQ ID NO: 9), and a suitable non-peptidic polyanion, e.g. 50 kDa PAA, by LBL at or near neutral pH. Each polymer is dissolved in a low ionic strength buffer at neutral pH to a final concentration of about 1 mg/mL; the multilayer film is built on a clean substrate, e.g., glass, quartz or silicon dioxide; if the substrate has a net negative charge, as in the case of quartz, the polycation is deposited first; a rinse step is used to remove loosely-bound polyelectrolyte, as in the usual electrostatic LBL methodology; then the polyanion is deposited from the same buffer at the same concentration; in this way any number of layers is deposited. The result is a multilayer film with alternating layers of designed polycationic peptide and PAA. A closely related example is provided by Shchukin et al. (2004) *J. Am. Chem. Soc.*, who have studied chondroitin sulfate/poly(L-arginine) films. Poly(L-arginine) is not a designed polycation. Another closely related example is provided by Blacklock et al. (2006) *Biomaterials*, who have studied designed polycationic peptide/polyribonucleic acid or polydeoxyribonucleic acid films. The polynucleic acid, which is polycationic under usual solution conditions, is substituted for some other type of polycation. The films were assembled under conditions where the polypeptide had a high net positive charge and the polynucleic acid a high net negative charge.

A designed polyanionic peptide multilayer film containing a non-peptidic polycation, in this case poly(allylamine hydrochloride) (PAH). The polypeptide film is made of a suitable designed peptidic polyanion, e.g., EVEGECEVEVEG-ECEVEVEGECEVEVEGECEY (SEQ ID NO: 10), and a suitable non-peptidic polycation, e.g. 50 kDa PAH, by LBL at or near neutral pH. Each polymer is dissolved in a low ionic strength buffer at neutral pH to a final concentration of about 1 mg/mL; the multilayer film is built on a clean substrate, e.g., glass, quartz or silicon dioxide; if the substrate has a net negative charge, as in the case of quartz, the polycation is deposited first; a rinse step is used to remove loosely-bound polyelectrolyte, as in the usual electrostatic LBL methodology; then the polyanion is deposited from the same buffer at the same concentration; in this way any number of layers is deposited. The result is a multilayer film with alternating layers of designed polyanionic peptide and PAH.

A designed polycationic peptide multilayer film containing a non-peptidic polyanion, in this case a nucleic acid, either DNA or RNA. The film is made of a suitable designed peptidic polycation, e.g., KVKGKCKVKVKGKCK-VKVKGKCKVKVKGKCKY (SEQ ID NO: 9), and a suitable non-peptidic polyanion, e.g., a plasmid encoding a gene of interest or interference RNA. Each polymer is dissolved in a low ionic strength buffer at neutral pH to a final concentration of about 1 mg/mL; the multilayer film is built on a clean substrate, e.g., glass, quartz or silicon dioxide; if the substrate has a net negative charge, as in the case of quartz, the polycation is deposited first; a rinse step is used to remove loosely-bound polyelectrolyte, as in the usual electrostatic LBL methodology; then the polyanion is deposited from the same buffer at the same concentration; in this way any number of layers is deposited. The result is a multilayer film with alternating layers of designed polycationic peptide and nucleic acid.

There are numerous possible advantages and applications of films with heterogeneous layers. For instance, films made of designed peptides and carbohydrates might show advantageous tensile or viscoelastic properties in addition to specific biofunctionality related to details of peptide structure. Films made of peptides and nucleic acids might be useful for delivery of nucleic acids, for example, in gene therapy or as a vaccine.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Other embodiments of the invention are possible and modifications may be made without departing from the spirit and scope of the invention. Therefore, the detailed description above is not meant to limit the invention. Rather, the scope of the invention is defined by the appended claims.

The invention claimed is:

1. A multilayer film comprising a plurality of layers of polyelectrolytes, wherein adjacent layers are oppositely charged,
  wherein a first layer comprises a first layer polypeptide comprising one or more first amino acid sequence motifs,
    wherein the one or more first amino acid sequence motifs has a length of 5 to 15 amino acids residues, and wherein the balance of charge in the first amino acid sequence motif at pH 7 is greater than or equal to approximately one-half of the length of the first amino acid sequence motif,
  wherein the first layer polypeptide is not a homopolymer and is not a branched polypeptide, is at least 15 amino acid residues long, and has a balance of charge at pH 7 greater than or equal to approximately one-half of the total length of the first layer polypeptide, and
  wherein a second layer comprises a second layer polyelectrolyte having a charge opposite that of the first layer polypeptide,
  wherein the second layer polyelectrolyte is not a polypeptide.

2. The multilayer film of claim 1, wherein the second layer polyelectrolyte comprises hyaluronate, alginate, poly(allylamine hydrochloride), poly(diallyldimethylammonium chloride), poly(acrylic acid), poly(vinyl sulfate), a nucleic acid, or a combination comprising one or more of the foregoing polyelectrolytes.

3. The multilayer film of claim 1, wherein the film is in the form of a microcapsule.

4. The multilayer film of claim 3, wherein the microcapsule comprises a core, and the core comprises a protein, or a drug.

5. The multilayer film of claim 4, wherein the protein or drug is in crystallized form.

6. The multilayer film of claim 4, wherein the protein or drug is in liquid form.

7. The multilayer film of claim 1, wherein the first layer polypeptide comprises two amino acid sequence motifs; wherein the two amino acid sequence motifs are covalently joined by a glycine linker, or a proline linker; and wherein the two amino acid sequence motifs are the same or different.

8. The multilayer film of claim 1, comprising at least 5 pairs of alternately charged layers.

9. The multilayer film of claim 1, having a thickness of 20 nm to 50 nm.

10. The multilayer film of claim 1, wherein the film is formed on a substrate.

11. The multilayer film of claim 10, wherein the substrate comprises a medical implant.

12. The multilayer film of claim 1, wherein at least one of the amino acid sequence motifs of the first layer polypeptide is present in the human proteome.

13. A method of making a multilayer film comprising a plurality of layers of polyelectrolytes, wherein adjacent layers are oppositely charged, the method comprising:
  depositing a first layer polyelectrolyte on a surface of a substrate to form a first layer; and
  depositing a second layer polyelectrolyte on the first layer polyelectrolyte to form a second layer, wherein the second layer polyelectrolyte has a charge opposite that of the first layer polyelectrolyte
  wherein the first layer polyelectrolyte, the second layer polyelectrolyte, or both, comprises a polypeptide;
  wherein the polypeptide comprises one or more amino acid sequence motifs,
    wherein the one or more amino acid sequence motifs have a length of 5 to 15 amino acids residues, and wherein the balance of charge in the amino acid sequence motif at pH 7 is greater than or equal to approximately one-half of the length of the amino acid sequence motif,
  wherein the polypeptide is not a homopolymer and is not a branched polypeptide, is at least 15 amino acid residues long, and has a balance of charge at pH 7 greater than or equal to approximately one-half of the total length of the polypeptide.

* * * * *

SEQUENCE LISTING

<160> NUMBER OF SEQ ID NOS: 10

<210> SEQ ID NO 1
<211> LENGTH: 32
<212> TYPE: PRT
<213> ORGANISM: Artificial
<220> FEATURE:
<223> OTHER INFORMATION: The sequence was designed de novo and
      synthesized.

<400> SEQUENCE: 1

Tyr Arg Arg Arg Arg Ser Val Gln Gly Arg Arg Arg Arg Ser Val Gln
1               5                   10                  15

Gly Arg Arg Arg Arg Ser Val Gln Gly Arg Arg Arg Arg Ser Val Gln
            20                  25                  30

<210> SEQ ID NO 2
<211> LENGTH: 32
<212> TYPE: PRT
<213> ORGANISM: Artificial
<220> FEATURE:
<223> OTHER INFORMATION: The sequence was designed de novo and
      synthesized.

```
<400> SEQUENCE: 2

Tyr Glu Glu Asp Glu Cys Gln Asp Gly Glu Glu Asp Glu Cys Gln Asp
1               5                   10                  15

Gly Glu Glu Asp Glu Cys Gln Asp Gly Glu Glu Asp Glu Cys Gln Asp
            20                  25                  30

<210> SEQ ID NO 3
<211> LENGTH: 48
<212> TYPE: PRT
<213> ORGANISM: Artificial
<220> FEATURE:
<223> OTHER INFORMATION: The sequence was designed de novo and
      synthesized.

<400> SEQUENCE: 3

Tyr Arg Arg Arg Arg Ser Val Gln Gly Arg Arg Arg Arg Ser Val Gln
1               5                   10                  15

Gly Arg Arg Arg Arg Ser Val Gln Gly Arg Arg Arg Arg Ser Val Gln
            20                  25                  30

Gly Arg Arg Arg Arg Ser Val Gln Gly Arg Arg Arg Arg Ser Val Gln
        35                  40                  45

<210> SEQ ID NO 4
<211> LENGTH: 48
<212> TYPE: PRT
<213> ORGANISM: Artificial
<220> FEATURE:
<223> OTHER INFORMATION: The sequence was designed de novo and
      synthesized.

<400> SEQUENCE: 4

Tyr Glu Glu Asp Glu Cys Gln Asp Gly Glu Glu Asp Glu Cys Gln Asp
1               5                   10                  15

Gly Glu Glu Asp Glu Cys Gln Asp Gly Glu Glu Asp Glu Cys Gln Asp
            20                  25                  30

Gly Glu Glu Asp Glu Cys Gln Asp Gly Glu Glu Asp Glu Cys Gln Asp
        35                  40                  45

<210> SEQ ID NO 5
<211> LENGTH: 32
<212> TYPE: PRT
<213> ORGANISM: Artificial
<220> FEATURE:
<223> OTHER INFORMATION: The sequence was designed de novo and
      synthesized.

<400> SEQUENCE: 5

Tyr Lys Cys Lys Gly Lys Val Lys Val Lys Cys Lys Gly Lys Val Lys
1               5                   10                  15

Val Lys Cys Lys Gly Lys Val Lys Val Lys Cys Lys Gly Lys Val Lys
            20                  25                  30

<210> SEQ ID NO 6
<211> LENGTH: 32
<212> TYPE: PRT
<213> ORGANISM: Artificial
<220> FEATURE:
<223> OTHER INFORMATION: The sequence was designed de novo and
      synthesized.
```

```
<400> SEQUENCE: 6

Tyr Glu Cys Glu Gly Glu Val Glu Val Glu Cys Glu Gly Glu Val Glu
1               5                   10                  15

Val Glu Cys Glu Gly Glu Val Glu Val Glu Cys Glu Gly Glu Val Glu
            20                  25                  30

<210> SEQ ID NO 7
<211> LENGTH: 32
<212> TYPE: PRT
<213> ORGANISM: Artificial
<220> FEATURE:
<223> OTHER INFORMATION: The sequence was designed de novo and
      synthesized.

<400> SEQUENCE: 7

Tyr Lys Gly Lys Lys Ser Cys His Gly Lys Gly Lys Lys Ser Cys His
1               5                   10                  15

Gly Lys Gly Lys Lys Ser Cys His Gly Lys Gly Lys Lys Ser Cys His
            20                  25                  30

<210> SEQ ID NO 8
<211> LENGTH: 23
<212> TYPE: PRT
<213> ORGANISM: Artificial
<220> FEATURE:
<223> OTHER INFORMATION: The sequence was designed de novo and
      synthesized.

<400> SEQUENCE: 8

Asp Ser His Ala Lys Arg His His Gly Tyr Lys Arg Lys His Glu Lys
1               5                   10                  15

His His Ser His Arg Gly Tyr
            20

<210> SEQ ID NO 9
<211> LENGTH: 32
<212> TYPE: PRT
<213> ORGANISM: Artificial
<220> FEATURE:
<223> OTHER INFORMATION: The sequence was designed de novo and
      synthesized.

<400> SEQUENCE: 9

Lys Val Lys Gly Lys Cys Lys Val Lys Val Lys Gly Lys Cys Lys Val
1               5                   10                  15

Lys Val Lys Gly Lys Cys Lys Val Lys Val Lys Gly Lys Cys Lys Tyr
            20                  25                  30

<210> SEQ ID NO 10
<211> LENGTH: 32
<212> TYPE: PRT
<213> ORGANISM: Artificial
<220> FEATURE:
<223> OTHER INFORMATION: The sequence was designed de novo and
      synthesized.

<400> SEQUENCE: 10

Glu Val Glu Gly Glu Cys Glu Val Glu Val Glu Gly Glu Cys Glu Val
1               5                   10                  15

Glu Val Glu Gly Glu Cys Glu Val Glu Val Glu Gly Glu Cys Glu Tyr
            20                  25                  30
```